(12) United States Patent
Yamamoto et al.

(10) Patent No.: US 8,143,052 B2
(45) Date of Patent: Mar. 27, 2012

(54) PROCESS FOR PREPARING OPTICALLY ACTIVE (S OR R)-α AMINO ACID AND (R OR S)-α AMINO ACID ESTER IN ONE PHASE ORGANIC REACTION MEDIUM

(75) Inventors: Yasuhito Yamamoto, Ube (JP); Hiroyuki Miyata, Ube (JP); Tadayoshi Konegawa, Ube (JP)

(73) Assignee: UBE Industries, Ltd., Ube-Shi (JP)

( * ) Notice: Subject to any disclaimer, the term of this patent is extended or adjusted under 35 U.S.C. 154(b) by 1001 days.

(21) Appl. No.: 12/064,589

(22) PCT Filed: Aug. 25, 2006

(86) PCT No.: PCT/JP2006/316735
§ 371 (c)(1),
(2), (4) Date: Feb. 22, 2008

(87) PCT Pub. No.: WO2007/023948
PCT Pub. Date: Mar. 1, 2007

(65) Prior Publication Data
US 2009/0042260 A1    Feb. 12, 2009

(30) Foreign Application Priority Data
Aug. 25, 2005 (JP) .................. 2005-243730

(51) Int. Cl.
C12P 41/00 (2006.01)
(52) U.S. Cl. ...................................... 435/280
(58) Field of Classification Search .................. None
See application file for complete search history.

(56) References Cited

U.S. PATENT DOCUMENTS

2006/0178433 A1* 8/2006 Yamamoto et al. ........... 514/538
2008/0038785 A1* 2/2008 Konegawa et al. ........... 435/106

FOREIGN PATENT DOCUMENTS

| EP | 1 621 529 A1 | 2/2006 |
| WO | WO-97/06162 A1 | 2/1997 |
| WO | WO-98/03473 A1 | 1/1998 |
| WO | WO-2004/063198 A1 | 7/2004 |
| WO | WO 2004/083163 | * 9/2004 |
| WO | WO-2004-083163 A1 | 9/2004 |
| WO | WO-2004/084812 A3 | 10/2004 |
| WO | WO-2005/051304 A3 | 6/2005 |
| WO | WO 2006/038698 | * 4/2006 |

OTHER PUBLICATIONS

Fukunaga et al., "Preparation of the gemini detergent-lipase complexes and their high enzymatic activities in the transesterifications in homogeneous organic solvents", Biotechnology Letters 20 (12) : 1161-1165 (1998).*
Kijima et al., "Facile Optical Resolution of Amino Acid Esters via Hydrolysis by an Industrial Enzyme in Organic Solvents", J. Chem. Tech. Biotechnol. 59 : 61-65 (1994).*
Miyazawa T. at al., Tetrahedron: Asymmetry, vol. 8, No. 3, (1997), pp. 367-370.
Tadashi Ema et al., Journal of Synthetic Organic Chemistry, Japan, vol. 58, No. 7, (2000), pp. 691-698.
Alain Daugan et al., J. Med. Chem. 2003, 46, pp. 4533-4542.
Jer-Yiing Joung et al., Chirality, 8, (1996), pp. 418-422.
Chin-Shih Chen et al., J. Am. Chem. Soc. 1982, 104, pp. 7294-7299.
Hideo Kise et al., Biotechnology letters, vol. 13, No. 5, (1991), pp. 317-322.
Extended European Search Report in European Application No. 06796808.1 mailed Sep. 27, 2010.
Houng et al., "Kinetic Resolution of Amino Acids Esters Catalyzed by Lipases," Chirality, vol. 8, 1996, XP-002600449, pp. 418-422.
Houng et al., "Lipase-Catalysed Kinetic Resolution of Ethyl D,L-2-amino-4-phenylbutyrate by Hydrolysis," Biotechnology Techniques, vol. 10, No. 5, May 1996, XP-002600448, pp. 353-358.
"Kagaku Jiten (Chemical Dictionary)", published by Tokyo Kagaku Dozin Co., Ltd., (2000), pp. 948.

* cited by examiner

Primary Examiner — Sandra Saucier
(74) Attorney, Agent, or Firm — Birch, Stewart, Kolasch & Birch, LLP

(57) ABSTRACT

The present invention discloses a process for preparing an optically active (S or R)-α-amino acid represented by the formula (II):

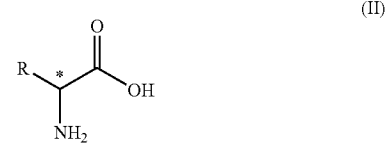

wherein R represents an alkyl group, alkenyl group, alkynyl group, cycloalkyl group, aralkyl group, heteroaralkyl group, aryl group or heteroaryl group, each of which may have a substituent(s), and * represents an asymmetric carbon atom, and an optically active (R or S)-α-amino acid ester represented by the formula (III):

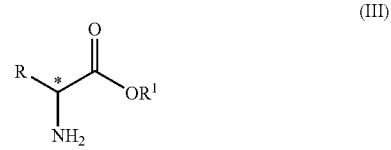

wherein $R^1$ represents an alkyl group which may have a substituent(s), and * represents an asymmetric carbon atom, provided that it has an opposite absolute configuration to that of the compound of the formula (II), which comprises selectively reacting water with one of enantiomers of an α-amino acid ester which is a racemic mixture and represented by the formula (I):

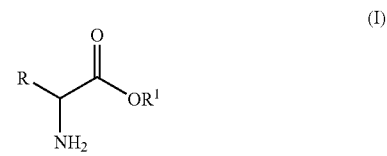

wherein R and $R^1$ have the same meanings as defined above,
in the presence of a lipase or a protease in an organic solvent.

17 Claims, No Drawings

PROCESS FOR PREPARING OPTICALLY ACTIVE (S OR R)-α AMINO ACID AND (R OR S)-α AMINO ACID ESTER IN ONE PHASE ORGANIC REACTION MEDIUM

TECHNICAL FIELD

The present invention relates to a process for simultaneously preparing an optically active (S or R)-α-amino acid and its antipode ester, an optically active (R or S)-α-amino acid ester, from an α-amino acid ester (racemic mixture). These optically active α-amino acid and an ester thereof are useful compounds as a starting material or a synthetic intermediate of a natural substance having physiological activity or a medicine (for example, see Non-Patent Literature 1, and Patent Literatures 1 to 5).

BACKGROUND ART

Heretofore, as a process for preparing an optically active α-amino acid and an ester thereof by an enantio-selective hydrolysis reaction using a lipase, there has been disclosed a method in which, for example, only one of enantiomers of various kinds of amino acid esters is selectively hydrolyzed in water in the presence of a porcine pancreatic lipase, a lipase originated from *Burkholderia cepacia* (*Pseudomonas cepacia*), or a lipase originated from *Rhizopus* to obtain an optically active (S)-amino acid and an optically active (R)-amino acid ester (for example, see Non-Patent Literature 2).

However, according to this method, a large amount of an enzyme has been used, and there are problems that an E value which is an index of selectivity between enantiomers is generally low. When an optically active carboxylic acid which is a product is water-soluble, it is difficult to recover 100% of the product from the aqueous solution after completion of the reaction, and yet, in the presence of a large amount of water, lowering in optical purity occurs due to self-hydrolysis reaction of the substrate. Incidentally, the E value has widely been utilized as an index of selectivity of kinetic optical resolution (for example, see Non-Patent Literature 3.).

Also, as a conventional process for preparing an optically active α-amino acid and an ester thereof by an enantio-selective hydrolysis reaction using a protease, there is disclosed, for example, a method in which one of the enantiomers of tyrosine ethyl ester is selectively hydrolyzed in an acetonitrile-water mixed solvent in the presence of α-chymotrypsin, subtilisin Carlsberg and subtilisin BPN' to obtain an optically active (S)-tyrosine and an optically active (R)-tyrosine ethyl ester (for example, see Non-Patent Literature 4). Here, various reactions were carried out by changing a water content in acetonitrile, and the most preferred results can be obtained in an amount of 5 to 10% (v/v) of water based on acetonitrile which is a solvent.

However, in the above-mentioned reaction systems, no hydrolysis is carried out with a system in which a water content is extremely little as 10 equivalent or less based on an amount of the substrate, nor referred to at all. In the system used in this case, an amount of water used as a substrate is still large, it is difficult to completely inhibit self-hydrolysis of the amino acid ester, and a substrate concentration based on the solvent is low so that it is not an industrially preferred method.

Non-Patent Literature 1: J. Med. Chem., 46, 4533 (2003)
Non-Patent Literature 2: Chirality, 8, 418 (1996)
Non-Patent Literature 3: J. Am. Chem. Soc., 104, 7294 (1982)
Non-Patent Literature 4: Biotechnology Letters, 13, (5), 317 (1991)
Non-Patent Literature 5: "Chemical Dictionary", published by Tokyo Kagaku Dojin Co., Ltd., p. 948 (2000)
Patent Literature 1: WO 9706162
Patent Literature 2: WO 2004063198
Patent Literature 3: WO 2004084812
Patent Literature 4: WO 9803473
Patent Literature 5: WO 2005051304

DISCLOSURE OF THE INVENTION

Problems to be Solved by the Invention

An object of the present invention is to solve the above-mentioned problems, and to provide a process for preparing an optically active (S or R)-α-amino acid and its antipode ester, an optically active (R or S)-α-amino acid ester, simultaneously from an α-amino acid ester (racemic mixture) according to hydrolysis using an enzyme with a simple and easy method, and a high E value.

Means to Solve the Problems

Heretofore, a preparation of an optically active α-amino acid by enantio-selective hydrolysis of an α-amino acid ester (racemic mixture) is generally carried out by a method in which, a large amount of water and a racemic β-amino acid ester are reacted in a solvent mainly comprising water in the presence of a hydrolase. This is because, in hydrolysis of a racemic α-amino acid ester which is a substrate, it has been considered that a larger amount of water proceeds the reaction. The present inventors have earnestly studied to solve the problems as previously mentioned, and as a result, they have found out a novel reaction system, which can substantially and completely inhibit self-hydrolysis of a substrate (β-amino acid ester) which is easily hydrolyzed by water, which causes lowering in an optical purity, and can completely recover the optically active α-amino acid which is generally considered to be difficult to obtain solely due to its water-solubility, which is improved in yield, selectivity, operability, etc. as compared with the conventional techniques, and which is more advantageous as an industrial preparation method, which can be accomplished by reacting water and an α-amino acid ester (racemic mixture) in an organic solvent in the presence of a lipase or a protease.

The present invention relates to a process for preparing an optically active (S or R)-α-amino acid represented by the formula (II):

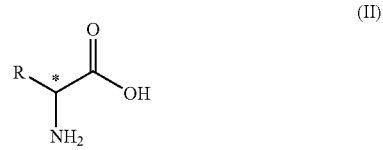

(II)

wherein R represents an alkyl group, an alkenyl group, an alkynyl group, a cycloalkyl group, an aralkyl group, a heteroarylalkyl group, an aryl group or a heteroaryl group, each of which may have a substituent(s), and * represents an asymmetric carbon atom, and an optically active (R or S)-α-amino acid ester represented by the formula (III):

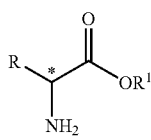

(III)

wherein R has the same meaning as defined above, R¹ represents an alkyl group which may have a substituent(s), and * represents an asymmetric carbon atom, provided that it has an opposite absolute configuration to that of the compound of the formula (II),
which comprises selectively reacting water with one of enantiomers of an α-amino acid ester which is a racemic mixture and represented by the formula (I):

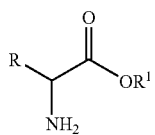

(I)

wherein R and R¹ have the same meanings as defined above,
in the presence of a lipase or a protease in an organic solvent.

The present invention also relates to a process for preparing an acid salt of an optically active (R or S)-α-amino acid ester, which comprises separating each of the optically active (S or R)-α-amino acid represented by the above-mentioned formula (II):

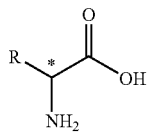

(II)

wherein R has the same meaning as defined above, and * represents an asymmetric carbon atom,
and the optically active (R or S)-α-amino acid ester represented by the above-mentioned formula (III):

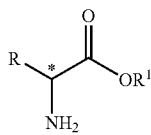

(III)

wherein R and R¹ have the same meanings as defined above, and * represents an asymmetric carbon atom, provided that it has an opposite absolute configuration to that of the compound of the formula (II),
formed by the above-mentioned reaction from a mixture thereof, and reacting the resulting optically active (R or S)-α-amino acid ester with an acid.

Effects of the Invention

According to the present invention, it can be provided a process for preparing an optically active (S or R)-α-amino acid and its antipode ester, an optically active (R or S)-α-amino acid ester, simultaneously from an α-amino acid ester (racemic mixture) by a hydrolysis reaction using an enzyme according to a simple and easy method with a high E value.

BEST MODE FOR CARRYING OUT THE INVENTION

R in Compound (I) represents an alkyl group, alkenyl group, alkynyl group, cycloalkyl group, aralkyl group, heteroarylalkyl group, aryl group or heteroaryl group, each of which may have a substituent(s).

The alkyl group of the alkyl group which may have a substituent(s) in the above-mentioned R is a linear or branched alkyl group having 1 to 10 carbon atoms, and there may be mentioned, for example, an alkyl group such as a methyl group, ethyl group, propyl group, butyl group, pentyl group, hexyl group, heptyl group, octyl group, nonyl group and decyl group, etc., preferably an alkyl group having 1 to 8 carbon atoms such as a methyl group, ethyl group, n-propyl group, isopropyl group, n-butyl group and n-octyl group, etc., more preferably an alkyl group having 1 to 2 carbon atoms such as a methyl group and ethyl group, etc. Incidentally, these groups contain various kinds of isomers.

The substituent(s) for the alkyl group which may have a substituent(s) may be mentioned, for example, a halogen atom such as a fluorine atom, chlorine atom, bromine atom, iodine atom, etc.; a hydroxyl group; an alkoxyl group having 1 to 4 carbon atoms such as a methoxyl group, ethoxyl group, propoxyl group, butoxyl group, etc.; an amino group; and a dialkylamino group which is disubstituted by alkyl groups having 1 to 6 carbon atoms such as a dimethylamino group, diethylamino group, etc.; a cyano group; and a nitro group, preferably a fluorine atom, chlorine atom, hydroxy group, amino group and dialkylamino group.

Such an alkyl group having the above-mentioned substituent(s) may be specifically mentioned, for example, a fluoromethyl group, chloromethyl group, hydroxymethyl group, methoxymethyl group, aminomethyl group, dimethylaminomethyl group, 2-chloroethyl group, 2,2-dichloroethyl group, 2-hydroxyethyl group and 2-cyanoethyl group, etc., preferably a fluoromethyl group, chloromethyl group, hydroxymethyl group, aminomethyl group, dimethylaminomethyl group, 2-chloroethyl group and 2-cyanoethyl group.

The alkenyl group of the alkenyl group which may have a substituent(s) in the above-mentioned R is mentioned, for example, an alkenyl group having 2 to 10 carbon atoms such as a vinyl group, propenyl group, butenyl group, pentenyl group, hexenyl group, heptenyl group, octenyl group, nonenyl group and decenyl group, etc., preferably an alkenyl group having 2 to 5 carbon atoms such as a vinyl group, propenyl group, butenyl group and pentenyl group, etc., more preferably an alkenyl group having 2 to 3 carbon atoms such as a vinyl group, 1-propenyl group and 2-propenyl group, etc. Incidentally, these groups contain various kinds of isomers.

The substituent(s) for the alkenyl group which may have a substituent(s) may be mentioned, for example, a halogen atom such as a fluorine atom, chlorine atom, bromine atom, iodine atom, etc.; a hydroxyl group; an alkoxyl group having 1 to 4 carbon atoms such as a methoxyl group, ethoxyl group, propoxyl group, butoxyl group, etc.; amino group; and a dialkylamino group which is disubstituted by alkyl groups having 1 to 6 carbon atoms such as a dimethylamino group, diethylamino group, etc.; a cyano group; and a nitro group, preferably a fluorine atom, chlorine atom, hydroxy group, amino group and dialkylamino group.

Such an alkenyl group having the above-mentioned substituent(s) may be specifically mentioned, for example, a 1-fluoroethenyl group, 1-chloroethenyl group, 1-hydroxyethenyl group, 1-methoxyethenyl group, 1-aminoethenyl group, 1-cyanoethenyl group, 2-fluoroethenyl group, 2-chloroethenyl group, 2-hydroxyethenyl group, 2-methoxyethenyl group, 2-aminoethenyl group, 2-cyanoethenyl group, 1,2-dimethylaminoethenyl group, 1-fluoro-2-propenyl group, 1-chloro-2-propenyl group, 1-hydroxy-2-propenyl group, 1-methoxy-2-propenyl group, 1-amino-2-propenyl group, 1-cyano-2-propenyl group, 3-fluoro-1-propenyl group, 3-chloro-1-propenyl group, 3-hydroxy-2-propenyl group, 3-methoxy-2-propenyl group, 3-amino-2-propenyl group, 2-cyano-2-propenyl group, 3,3-dimethylamino-2-propenyl group and 3,3-dichloro-2-propenyl group, etc., preferably a 1-fluoroethenyl group, 1-chloroethenyl group, 1-hydroxyethenyl group, 1-aminoethenyl group, 1-cyanoethenyl group, 1-fluoro-2-propenyl group, 1-chloro-2-propenyl group and 1-cyano-2-propenyl group.

The alkynyl group of the alkynyl group which may have a substituent(s) in the above-mentioned R may be mentioned, for example, an alkynyl group having 2 to 10 carbon atoms such as an ethynyl group, propynyl group, butynyl group, pentynyl group, hexynyl group, heptynyl group, octynyl group, nonynyl group and decynyl group, etc., preferably an alkynyl group having 2 to 5 carbon atoms such as an ethynyl group, propynyl group, butynyl group and pentynyl group, etc., more preferably an alkynyl group having 2 or 3 carbon atoms such as an ethynyl group, 1-propynyl group and 2-propynyl group, etc. Incidentally, these groups contain various kinds of isomers.

The substituent(s) for the alkynyl group which may have a substituent(s) may be mentioned, for example, a halogen atom such as a fluorine atom, chlorine atom, bromine atom, iodine atom, etc.; a hydroxyl group; an alkoxyl group having 1 to 4 carbon atoms such as a methoxyl group, ethoxyl group, propoxyl group, butoxyl group, etc.; an amino group; a dialkylamino group which is disubstituted by alkyl groups having 1 to 6 carbon atoms such as a dimethylamino group, diethylamino group, etc.; a cyano group; and a nitro group, preferably a fluorine atom, chlorine atom, hydroxy group, amino group and dialkylamino group.

Such an alkynyl group which may have a substituent(s) may be specifically mentioned, for example, a 2-fluoroethynyl group, 2-chloroethynyl group, 2-hydroxy-ethynyl group, 2-methoxyethynyl group, 2-aminoethynyl group, 2-cyanoethynyl group, 1-fluoro-2-propynyl group, 1-chloro-2-propynyl group, 1-hydroxy-2-propynyl group, 1-methoxy-2-propynyl group, 1-amino-2-propynyl group, 1-cyano-2-propynyl group, 1,1-dichloro-2-propynyl group and 1,1-diamino-2-propynyl group, etc., preferably a 2-fluoroethynyl group, 2-chloroethynyl group, 2-hydroxyethynyl group, 2-aminoethynyl group, 1-fluoro-2-propynyl group and 1,1-dichloro-2-propynyl group.

The cycloalkyl group of the cycloalkyl group which may have a substituent(s) in the above-mentioned R may be mentioned a cycloalkyl group having 3 to 10 carbon atoms, and there may be mentioned, for example, a cycloalkyl group such as a cyclopropyl group, cyclobutyl group, cyclopentyl group, cyclohexyl group, cycloheptyl group, cyclooctyl group, cyclononyl group and cyclodecyl group, etc. (Incidentally, these groups contain various kinds of isomers.), preferably a cycloalkyl group having 3 to 8 carbon atoms such as a cyclopropyl group, cyclobutyl group, cyclopentyl group, cyclohexyl group, cycloheptyl group and cyclooctyl group, etc., more preferably a cycloalkyl group having 3 to 6 carbon atoms such as a cyclopropyl group, cyclobutyl group, cyclopentyl group and cyclohexyl group, etc.

The substituent(s) for the cycloalkyl group which may have a substituent(s) may be mentioned an alkyl group having 1 to 6 carbon chain atoms, a halogen atom such as a fluorine atom, chlorine atom, bromine atom, iodine atom, etc.; a hydroxyl group; an alkoxyl group having 1 to 4 carbon atoms such as a methoxyl group, ethoxyl group, propoxyl group, butoxyl group, etc.; an amino group; a dialkylamino group which is disubstituted by alkyl groups having 1 to 6 carbon atoms such as a dimethylamino group, diethylamino group, etc.; a cyano group; and a nitro group, preferably a fluorine atom, chlorine atom, hydroxy group, amino group and dialkylamino group.

Such a cycloalkyl group which may have a substituent(s) may be specifically mentioned, for example, a 1-fluorocyclopropyl group, 2-chlorocyclopropyl group, 3-fluorocyclobutyl group, methoxycyclopropyl group, aminocyclopentyl group, dimethylaminocyclohexyl group, 2-chlorocyclopropyl group, 2,2-dichlorocyclohexyl group, 2-hydroxycyclobutyl group and 2-cyanocyclohexyl group, etc., preferably a 1-fluorocyclopropyl group and chlorocyclobutyl group.

The aralkyl group of the aralkyl group which may have a substituent(s) in the above-mentioned R may be mentioned, for example, an aralkyl group in which an alkyl group having 1 to 6 carbon atoms is substituted by an aryl group having 6 to 14 carbon atoms, such as a benzyl group, 1-naphthylmethyl group, 2-naphthylmethyl group, phenethyl group, phenylpropyl group and phenylbutyl group, etc., preferably an aralkyl group in which an alkyl group having 1 to 4 carbon atoms is substituted by an aryl group, such as a benzyl group, 1-naphthylmethyl group, 2-naphthylmethyl group, 1-phenethyl group, 2-phenethyl group, 3-phenylpropyl group and 3-phenylbutyl group, etc., particularly preferably an aralkyl group in which a methyl group is substituted by an aryl group, such as a benzyl group, 1-naphthylmethyl group, 2-naphthylmethyl group, etc. Incidentally, these groups contain various kinds of isomers.

The substituent(s) for the aralkyl group which may have a substituent(s) may be mentioned, for example, an alkyl group having 1 to 10 carbon atoms such as a methyl group, ethyl group, propyl group, butyl group, pentyl group, hexyl group, heptyl group, octyl group, nonyl group, decyl group, etc. (Incidentally, these groups contain various kinds of isomers.); a hydroxyl group; a nitro group; a halogen atom such as a fluorine atom, chlorine atom, bromine atom, iodine atom, etc.; an alkoxyl group having 1 to 10 carbon atoms such as a methoxyl group, ethoxyl group, propoxyl group, butoxyl group, pentyloxyl group, hexyloxyl group, heptyloxyl group, octyloxyl group, nonyloxyl group, decyloxyl group, etc. (Incidentally, these groups contain various kinds of isomers.); an aralkyloxyl group having 7 to 10 carbon atoms such as a benzyloxyl group, phenethyloxyl group, phenylpropoxyl group, etc. (Incidentally, these groups contain various kinds of isomers.); an aryloxyl group having 6 to 20 carbon atoms such as a phenyloxyl group, naphthyloxyl group, etc. (Incidentally, these groups contain various kinds of isomers.); an alkoxyalkoxyl group having 2 to 12 carbon atoms such as a methoxymethoxyl group, methoxyethoxyl group, etc. (Incidentally, these groups contain various kinds of isomers.); a monoalkylamino group such as a methylamino group, ethylamino group, etc. (Incidentally, these groups contain various kinds of isomers.); a dialkylamino group which is disubstituted by alkyl groups having 1 to 6 carbon atoms such as dimethylamino group, diethylamino group, etc. (Incidentally, these groups contain various kinds of isomers.); an acylamino group having 1 to 12 carbon atoms such as a formylamino group, acetylamino group, benzoylamino group, etc. (Incidentally, these groups contain various kinds of isomers.); a nitro group; a cyano group; and a halogenated alkyl group having 1 to 12 carbon atoms such as a trifluoromethyl group, etc.

As an aralkyl group having such a substituent(s), there may be specifically mentioned, for example, a 2-fluorobenzyl group, 3-fluorobenzyl group, 4-fluorobenzyl group, 3,4-difluorobenzyl group, 2,4-difluorobenzyl group, 2-chlorobenzyl group, 3-chlorobenzyl group, 4-chlorobenzyl group, 2,4-dichlorobenzyl group, 3,4-dichlorobenzyl group, 2-bromobenzyl group, 3-bromobenzyl group, 4-bromobenzyl group, 2,4-dibromobenzyl group, 3,4-dibromobenzyl group, 2-iodobenzyl group, 3-iodobenzyl group, 4-iodobenzyl group, 2,3-diiodobenzyl group, 3,4-diiodobenzyl group, 2-methylbenzyl group, 3-methylbenzyl group, 4-methylbenzyl group, 2-ethylbenzyl group, 3-ethylbenzyl group, 4-ethylbenzyl group, 2-hydroxybenzyl group, 3-hydroxybenzyl group, 4-hydroxybenzyl group, 2-methoxybenzyl group, 3-methoxybenzyl group, 4-methoxybenzyl group, 2,4-dimethoxybenzyl group, 3,4-dimethoxybenzyl group, 2-ethoxybenzyl group, 4-ethoxybenzyl group, 2-trifluoromethylbenzyl group, 4-trifluoromethylbenzyl group, 4-benzyloxybenzyl group, 2-nitrobenzyl group, 3-nitrobenzyl group, 4-nitrobenzyl group, 2-cyanobenzyl group, 3-cyanobenzyl group, 4-cyanobenzyl group, 4-dimethylaminobenzyl group, 4-formylaminobenzyl group, 2-acetylaminobenzyl group, 3-acetylaminobenzyl group, 4-acetylaminobenzyl group, 4-benzoylaminobenzyl group, 1-naphthylmethyl group, 2-naphthylmethyl group, 2-(2-fluorophenyl)ethyl group, 2-(3-fluorophenyl)ethyl group, 2-(4-fluorophenyl)ethyl group, 2-(3,4-difluorophenyl)ethyl group, 2-(2,4-difluorophenyl)ethyl group, 2-(2-chlorophenyl)ethyl group, 2-(3-chlorophenyl)ethyl group, 2-(4-chlorophenyl)ethyl group, 2-(2,4-dichlorophenyl)ethyl group, 2-(3,4-dichlorophenyl)ethyl group, 2-(2-bromophenyl)ethyl group, 2-(3-bromophenyl)ethyl group, 2-(4-bromophenyl)ethyl group, 2-(2,4-dibromophenyl)ethyl group, 2-(3,4-dibromophenyl)ethyl group, 2-(2-iodophenyl)ethyl group, 2-(3-iodophenyl)ethyl group, 2-(4-iodophenyl)ethyl group, 2-(2,3-diiodophenyl)ethyl group, 2-(3,4-diiodophenyl)ethyl group, 2-(2-tolyl)ethyl group, 2-(3-tolyl)ethyl group, 2-(4-tolyl)ethyl group, 2-(2-ethylphenyl)ethyl group, 2-(3-ethylphenyl)ethyl group, 2-(4-ethylphenyl)ethyl group, 2-(2-hydroxyphenyl)ethyl group, 2-(4-hydroxyphenyl)ethyl group, 2-(2-methoxyphenyl)ethyl group, 2-(3-methoxyphenyl)ethyl group, 2-(4-methoxyphenyl)ethyl group, 2-(2,4-dimethoxyphenyl)ethyl group, 2-(3,4-dimethoxyphenyl)ethyl group, 2-(2-ethoxyphenyl)ethyl group, 2-(4-ethoxyphenyl)ethyl group, 2-(2-trifluoromethylphenyl)ethyl group, 2-(4-trifluoromethylphenyl)ethyl group, 2-(2-benzyloxyphenyl)ethyl group, 2-(2-nitrophenyl)ethyl group, 2-(3-nitrophenyl)ethyl group, 2-(4-nitrophenyl)ethyl group, 2-(2-cyanophenyl)ethyl group, 2-(3-cyanophenyl)ethyl group, 2-(4-cyanophenyl)ethyl group, 2-(4-dimethylaminophenyl)ethyl group, 2-(4-formylaminophenyl)ethyl group, 2-(2-acetylaminophenyl)ethyl group, 2-(3-acetylaminophenyl)ethyl group, 2-(4-formylaminophenyl)ethyl group, 2-(4-benzoylaminophenyl)ethyl group, 3-(2-fluorophenyl)propyl group, 3-(4-fluorophenyl)propyl group, 3-(4-chlorophenyl)propyl group, 3-(4-bromophenyl)propyl group, 3-(4-iodophenyl)propyl group, 3-(2-chlorophenyl)propyl group, 3-(2-methoxyphenyl)propyl group, 3-(4-methoxyphenyl)propyl group, 3-(3,4-dimethoxyphenyl)propyl group, 3-(4-trifluoromethylphenyl)propyl group, 3-(2-trifluoromethylphenyl)propyl group, 3-(4-nitrophenyl)propyl group, 3-(4-cyanophenyl)propyl group and 3-(4-acetylaminophenyl)propyl group, etc., preferably a 2-fluorobenzyl group, 3-fluorobenzyl group, 4-fluorobenzyl group, 2-chlorobenzyl group, 3-chlorobenzyl group, 4-chlorobenzyl group, 2-bromobenzyl group, 3-bromobenzyl group, 4-bromobenzyl group, 2-iodobenzyl group, 3-iodobenzyl group, 4-iodobenzyl group, 2-methylbenzyl group, 3-methylbenzyl group, 4-methylbenzyl group, 2-hydroxybenzyl group, 4-hydroxybenzyl group, 2-methoxybenzyl group, 3-methoxybenzyl group, 4-methoxybenzyl group, 3,4-dimethoxybenzyl group, 2-trifluoromethylbenzyl group, 4-trifluoromethylbenzyl group, 4-benzyloxybenzyl group, 2-nitrobenzyl group, 3-nitrobenzyl group, 4-nitrobenzyl group, 2-cyanobenzyl group, 3-cyanobenzyl group, 4-cyanobenzyl group, 4-formylaminobenzyl group, 3-acetylaminobenzyl group, 4-acetylaminobenzyl group, 4-benzoylaminobenzyl group, 1-naphthylmethyl group, 2-naphthylmethyl group, 2-(2-fluorophenyl)ethyl group, 2-(3-fluorophenyl)ethyl group, 2-(4-fluorophenyl)ethyl group, 2-(2-chlorophenyl)ethyl group, 2-(3-chlorophenyl)ethyl group, 2-(4-chlorophenyl)ethyl group, 2-(2-bromophenyl)ethyl group, 2-(3-bromophenyl)ethyl group, 2-(4-bromophenyl)ethyl group, 2-(2-iodophenyl)ethyl group, 2-(3-iodophenyl)ethyl group, 2-(4-iodophenyl)ethyl group, 2-(2-tolyl)ethyl group, 2-(3-tolyl)ethyl group, 2-(4-tolyl)ethyl group, 2-(4-hydroxyphenyl)ethyl group, 2-(2-methoxyphenyl)ethyl group, 2-(3-methoxyphenyl)ethyl group, 2-(4-methoxyphenyl)ethyl group, 2-(3,4-dimethoxyphenyl)ethyl group, 2-(2-trifluoromethylphenyl)ethyl group, 2-(4-trifluoromethylphenyl)ethyl group, 2-(4-benzyloxyphenyl)ethyl group, 2-(2-nitrophenyl)ethyl group, 2-(4-nitrophenyl)ethyl group, 2-(2-cyanophenyl)ethyl group, 2-(4-cyanophenyl)ethyl group, 2-(2-acetylaminophenyl)

ethyl group and 2-(4-acetylaminophenyl)ethyl group), particularly preferably 2-fluorobenzyl group, 4-fluorobenzyl group, 2-chlorobenzyl group, 4-chlorobenzyl group, 2-bromobenzyl group, 4-bromobenzyl group, 2-iodobenzyl group, 4-iodobenzyl group, 2-methylbenzyl group, 4-methylbenzyl group, 4-hydroxybenzyl group, 2-methoxybenzyl group, 4-methoxybenzyl group, 3,4-dimethoxybenzyl group, 2-trifluoromethylbenzyl group, 4-trifluoromethylbenzyl group, 4-benzyloxybenzyl group, 2-nitrobenzyl group, 4-nitrobenzyl group, 2-cyanobenzyl group, 3-cyanobenzyl group, 4-cyanobenzyl group, 3-acetylaminobenzyl group, 4-acetylaminobenzyl group, 1-naphthylmethyl group and 2-naphthylmethyl group.

The heteroarylalkyl group of the heteroarylalkyl group which may have a substituent in the above-mentioned R may be mentioned, for example, a heteroarylalkyl group in which an alkyl group having 1 to 6 carbon atoms is substituted by a heteroaryl group having 6 to 14 carbon atoms, such as a 2-pyridylmethyl group, 3-pyridylmethyl group, 3-pyridylmethyl group, 2-thienylmethyl group, 3-thienylmethyl group, 2-imidazolyl group, 4-imidazolyl group, 2-thienylmethyl group, 3-indolylmethyl group, 2-pyridylethyl group, 2-thienylethyl group, 2-pyridylpropyl group, 2-pyridylbutyl group, etc., preferably a heteroarylalkyl group in which an alkyl group having 1 to 2 carbon atoms is substituted by a heteroaryl group, such as a 2-pyridylmethyl group, 2-thienylmethyl group, 3-indolylmethyl group, 2-pyridylethyl group, 2-thienylethyl group, etc., more preferably a heteroarylalkyl group in which a methyl group is substituted by a heteroarylalkyl group, such as a 2-pyridylmethyl group, 2-thienylmethyl group, 3-indolylmethyl group, etc. Incidentally, these groups contain various kinds of isomers.

The heteroaryl group of the heteroarylalkyl group which may have a substituent(s) in the above-mentioned R may be mentioned, for example, a 2-furyl group, 3-furyl group, 2-pyridyl group, 3-pyridyl group, 4-pyridyl group, 2-pyrrolyl group, 3-pyrrolyl group, 2-thienyl group, 3-thienyl group, 2-indolyl group, 3-indolyl group, 2-imidazolyl group, 4-imidazolyl group, 3-pyrazolyl group, 2-pyrimidyl group, 4-pyrimidyl group, 2-quinolyl group and 3-quinolyl group.

The substituent(s) for the heteroaryl group which may have a substituent(s) may be mentioned an alkyl group having 1 to 4 carbon atoms such as a methyl group, ethyl group, propyl group, butyl group, etc. (Incidentally, these groups contain various kinds of isomers.); a hydroxyl group; a halogen atom such as a chlorine atom, bromine atom, iodine atom, fluorine atom, etc.; an alkoxyl group having 2 to 4 carbon atoms such as an ethoxyl group, etc. (Incidentally, these groups contain various kinds of isomers.); an amino group; a nitro group; a cyano group; and a halogenated alkyl group having 1 to 4 carbon atoms such as a trifluoromethyl group, etc.

Such a heteroaryl group which may have a substituent(s) may be specifically mentioned, for example, a 2-(3-methyl)furyl group, 2-(4-methyl)furyl group, 2-(3-ethyl)furyl group, 2-(4-ethyl)furyl group, 2-(3-fluoro)furyl group, 2-(3-chloro)furyl group, 2-(3-hydroxy)furyl group, 2-(3-methoxy)furyl group, 2-(3-amino)furyl group, 2-(3-nitro)furyl group, 2-(3-cyano)furyl group, 2-(3-methyl)pyridyl group, 2-(4-methyl)pyridyl group, 2-(3-ethyl)pyridyl group, 2-(4-ethyl)pyridyl group, 2-(3-fluoro)pyridyl group, 2-(4-chloro)pyridyl group, 2-(3-hydroxy)pyridyl group, 2-(3-methoxy)pyridyl group, 2-(3-amino)pyridyl group, 2-(3-nitro)pyridyl group, 2-(3-cyano)pyridyl group, 2-(3,5-dichloro)pyridyl group, 3-(2-chloro)pyridyl group, 2-(3-methyl)pyrrolyl group and 2-(3-methyl)thienyl group, etc., preferably a 2-(3-methyl)furyl group, 2-(3-fluoro)furyl group, 2-(3-methyl)pyridyl group, 2-(3-fluoro)pyridyl group, 2-(3-nitro)pyridyl group, 2-(3-cyano)pyridyl group and 2-(3,5-dichloro)pyridyl group.

Such a heteroarylalkyl group which may have a substituent(s) may be specifically mentioned, for example, a 2-(3-methyl)furylmethyl group, 2-(4-methyl)furylmethyl group, 2-(3-ethyl)furylmethyl group, 2-(4-ethyl)furylmethyl group, 2-(3-fluoro)furylmethyl group, 2-(3-chloro)furylmethyl group, 2-(3-hydroxy)furylmethyl group, 2-(3-methoxy)furylmethyl group, 2-(3-amino)furylmethyl group, 2-(3-nitro)furylmethyl group, 2-(3-cyano)furylmethyl group, 2-(3-methyl)pyridylmethyl group, 2-(4-methyl)pyridylmethyl group, 2-(3-ethyl)pyridylmethyl group, 2-(4-ethyl)pyridylmethyl group, 2-(3-fluoro)pyridylmethyl group, 2-(4-chloro)pyridylmethyl group, 2-(3-hydroxy)pyridylmethyl group, 2-(3-methoxy)pyridylmethyl group, 2-(3-amino)pyridylmethyl group, 2-(3-nitro)pyridylmethyl group, 2-(3-cyano)pyridylmethyl group, 2-(3,5-dichloro)pyridylmethyl group, 3-(2-chloro)pyridylmethyl group, 2-(3-methyl)pyrrolylmethyl group and 2-(3-methyl)thienylmethyl group, etc., preferably a 2-(3-methyl)furylmethyl group, 2-(3-fluoro)furylmethyl group, 2-(3-methyl)pyridylmethyl group, 2-(3-fluoro)pyridylmethyl group, 2-(3-nitro)pyridyl group, 2-(3-cyano)pyridylmethyl group and 2-(3,5-dichloro)pyridylmethyl group.

The aryl group of the aryl group which may have a substituent(s) in the above-mentioned R may be mentioned a phenyl group, naphthyl group, anthryl group, phenanthryl group, biphenyl group and binaphthyl group.

The substituent(s) for the aryl group which may have a substituent(s) may be mentioned an alkyl group having 1 to 4 carbon atoms such as a methyl group, ethyl group, propyl group, butyl group, etc. (Incidentally, these groups contain various kinds of isomers.); a hydroxyl group; a halogen atom such as a chlorine atom, bromine atom, iodine atom, fluorine atom, etc.; an alkoxyl group having 2 to 4 carbon atoms such as an ethoxyl group, etc. (Incidentally, these groups contain various kinds of isomers.); an alkylenedioxyl group having 1 to 4 carbon atoms such as a methylenedioxyl group, etc.; a nitro group; a cyano group; and a halogenated alkyl group having 1 to 4 carbon atoms such as a trifluoromethyl group, etc.

Such an aryl group which may have a substituent(s) may be specifically mentioned, for example, a 2-tolyl group, 3-tolyl group, 4-tolyl group, 2,3-xylyl group, 2,6-xylyl group, 2,4-xylyl group, 3,4-xylyl group, mesityl group, 2-hydroxyphenyl group, 3-hydroxyphenyl group, 4-hydroxyphenyl group, 2,3-dihydroxyphenyl group, 2,4-dihydroxyphenyl group, 3,4-dihydroxyphenyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 2-iodophenyl group, 3-iodophenyl group, 4-iodophenyl group, 2-fluorophenyl group, 3-fluorophenyl group, 4-fluorophenyl group, 2,3-difluorophenyl group, 2,4-difluorophenyl group, 3,4-difluorophenyl group, 3-bromo-5-chloro-2-hydroxyphenyl group, 2-methoxyphenyl group, 3-methoxyphenyl group, 4-methoxyphenyl group, 2,3-dimethoxyphenyl group, 2,4-dimethoxyphenyl group, 3,4-dimethoxyphenyl group, 3,5-dimethoxyphenyl group, 3,4-methylenedioxyphenyl group, 4-ethoxyphenyl group, 4-butoxyphenyl group, 4-isopropoxyphenyl group, 1-phenoxyphenyl group, 4-benzyloxyphenyl group, 4-trifluoromethylphenyl group, 2-nitrophenyl group, 3-nitrophenyl group, 4-nitrophenyl group, 4-cyanophenyl group, 4-methoxycarbonylphenyl group, 1-naphthyl group and 2-naphthyl group, etc., preferably a phenyl group, 2-tolyl group, 3-tolyl group, 4-tolyl group, 2,3-xylyl group, 2-hydroxyphenyl group, 3-hydroxyphenyl group, 4-hydroxyphenyl group, 2,3-dihydroxyphenyl group, 2,4-dihydroxyphenyl group, 3,4-dihydroxyphenyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 2-iodophenyl group, 3-iodophenyl group, 4-iodophenyl group, 2-fluorophenyl group, 3-fluorophenyl group, 4-fluorophenyl group, 3,4-difluorophenyl group, 3-bromo-5-chloro-2-hydroxyphenyl group, 2-methoxyphenyl group, 3-methoxyphenyl group, 4-methoxyphenyl group, 2,3-dimethoxyphenyl group, 2,4-dimethoxyphenyl group, 3,4-dimethoxyphenyl group, 3,5-dimethoxyphenyl group, 3,4-methylenedioxyphenyl group, 4-ethoxyphenyl group, 4-trifluoromethylphenyl group, 4-nitrophenyl group, 4-cyanophenyl group, 1-naphthyl group and 2-naphthyl group, more preferably phenyl group, 2-tolyl group, 3-tolyl group, 4-tolyl group, 2,3-xylyl group, 4-hydroxyphenyl group, 3,4-dihydroxyphenyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 4-iodophenyl group, 2-fluorophenyl group, 3-fluorophenyl group, 4-fluorophenyl group, 3,4-difluorophenyl group, 2-iodophenyl group, 3-iodophenyl group, 4-iodophenyl group, 2-methoxyphenyl group, 3-methoxyphenyl group, 4-methoxyphenyl group, 2,3-dimethoxyphenyl group, 2,4-dimethoxyphenyl group, 3,4-dimethoxyphenyl group, 3,5-dimethoxyphenyl group, 3,4-methylenedioxyphenyl group, 4-trifluoromethylphenyl group, 4-nitrophenyl group, 1-naphthyl group, 2-naphthyl group and 3-pyridyl group, particularly preferably phenyl group, 2-tolyl group, 3-tolyl group, 4-tolyl group, 2,3-xylyl group, 2-chlorophenyl group, 3-chlorophenyl group, 4-chlorophenyl group, 2,3-dichlorophenyl group, 2,4-dichlorophenyl group, 3,4-dichlorophenyl group, 3,5-dichlorophenyl group, 2-bromophenyl group, 3-bromophenyl group, 4-bromophenyl group, 2-fluorophenyl group, 3-fluorophenyl group, 4-fluorophenyl group, 3,4-difluorophenyl group, 2-iodophenyl group, 3-iodophenyl group, 4-iodophenyl group, 2-methoxyphenyl group, 3-methoxyphenyl group, 4-methoxyphenyl group, 2,3-dimethoxyphenyl group, 3,4-dimethoxyphenyl group, 3,5-dimethoxyphenyl group or 3,4-methylenedioxyphenyl group.

The heteroaryl group of the heteroaryl group which may have a substituent(s) in the above-mentioned R may be mentioned, for example, a 2-furyl group, 3-furyl group, 2-pyridyl group, 3-pyridyl group, 4-pyridyl group, 2-pyrrolyl group, 3-pyrrolyl group, 2-thienyl group, 3-thienyl group, 2-indolyl group, 3-indolyl group, 2-imidazolyl group, 4-imidazolyl group, 3-pyrazolyl group, 2-pyrimidyl group, 4-pyrimidyl group and quinolyl group.

The substituent(s) for the heteroaryl group which may have a substituent(s) may be mentioned an alkyl group having 1 to 4 carbon atoms such as a methyl group, ethyl group, propyl group, butyl group, etc. (Incidentally, these groups contain various kinds of isomers.); a hydroxyl group; a halogen atom such as a chlorine atom, bromine atom, iodine atom, fluorine atom, etc.; an alkoxyl group having 2 to 4 carbon atoms such as an ethoxyl group, etc. (Incidentally, these groups contain various kinds of isomers.); an amino group; a nitro group; a cyano group; and a halogenated alkyl group having 1 to 4 carbon atoms such as a trifluoromethyl group, etc.

Such a heteroaryl group which may nave a substituent(s) may be specifically mentioned, for example, a 2-(3-methyl) furyl group, 2-(4-methyl)furyl group, 2-(3-ethyl)furyl group, 2-(4-ethyl)furyl group, 2-(3-fluoro)furyl group, 2-(3-chloro) furyl group, 2-(3-hydroxy)furyl group, 2-(3-methoxy)furyl group, 2-(3-amino)furyl group, 2-(3-nitro)furyl group, 2-(3-cyano)furyl group, 2-(3-methyl)pyridyl group, 2-(4-methyl) pyridyl group, 2-(3-ethyl)pyridyl group, 2-(4-ethyl)pyridyl group, 2-(3-fluoro)pyridyl group, 2-(4-chloro)pyridyl group, 2-(3-hydroxy)pyridyl group, 2-(3-methoxy)pyridyl group, 2-(3-amino)pyridyl group, 2-(3-nitro)pyridyl group, 2-(3-cyano)pyridyl group, 2-(3,5-dichloro)pyridyl group, 3-(2-chloro)pyridyl group, 2-(3-methyl)pyrrolyl group and 2-(3-methyl)thienyl group, etc., preferably a 2-(3-methyl)furyl group, 2-(3-fluoro)furyl group, 2-(3-methyl)pyridyl group, 2-(3-fluoro)pyridyl group, 2-(3-nitro)pyridyl group, 2-(3-cyano)pyridyl group and 2-(3,5-dichloro)pyridyl group.

$R^1$ in Compound (I) represents an alkyl group which may have a substituent(s).

The alkyl group of the alkyl group which may have a substituent(s) in the above-mentioned $R^1$ is a linear or branched alkyl group having 1 to 10 carbon atoms, and there may be mentioned, for example, an alkyl group such as a methyl group, ethyl group, propyl group, butyl group, pentyl group, hexyl group, heptyl group, octyl group, nonyl group and decyl group, preferably a linear or branched alkyl group having 1 to 6 carbon atoms such as a methyl group, ethyl group, n-propyl group, isopropyl group, n-butyl group, isobutyl group, sec-butyl group, n-pentyl group, n-hexyl group, etc., more preferably a linear or branched alkyl group having 1 to 4 carbon atoms such as a methyl group, ethyl group, n-propyl group, n-butyl group, isobutyl group, etc. Incidentally, these groups contain various kinds of isomers.

The substituent(s) for the alkyl group which may have a substituent(s) may be mentioned a halogen atom such as a fluorine atom, chlorine atom, bromine atom, iodine atom, etc.; a hydroxyl group; an alkoxy group having 1 to 4 carbon atoms such as a methoxyl group, ethoxyl group, propoxyl group, butoxyl group, etc.; a dialkylamino group which is di-substituted by an alkyl group having 1 to 6 carbon atoms such as a dimethylamino group, diethylamino group, etc.; and a cyano group, preferably a fluorine atom, chlorine atom, methoxyl group, ethoxyl group, hydroxyl group and cyano group, more preferably a fluorine atom, chlorine atom, methoxyl group and ethoxyl group.

Such an alkyl group which may have a substituent(s) may be specifically mentioned, for example, a 2-fluoroethyl group, 2-chloroethyl group, 2,2-difluoroethyl group, 2,2-dichloroethyl group, 2,2,2-trichloroethyl group, 2,2,2-trifluoroethyl group, 2-methoxyethyl group, 2-ethoxyethyl group, methoxymethyl group, 2-hydroxyethyl group, 2-cyanoethyl group, 2-bromoethyl group, 2-dimethylamino group, 2-chloropropyl group, 3-chloropropyl group, etc., preferably a 2-chloroethyl group, 2,2,2-trichloroethyl group, 2,2,2-trifluoroethyl group, methoxymethyl group, 2-methoxyethyl group and 2-ethoxyethyl group.

A lipase to be used in the reaction of the present invention is preferably a lipase derived from microorganisms which can be isolatable from an yeast or bacteria, more preferably a lipase originated from *Burkholderia cepacia* (*Pseudomonas cepacia*) (for example, AMANO PS (available from AMANO ENZYME CO.), etc.) can be used. Also, a protease to be used in the reaction of the present invention may be used, for example, a protease originated from pancreas of a vertebrate, *Aspergillus Olyzae, Aspergillus Melleus, Bacillus subtilis, Bacillus stearothermophilus*, etc.

Incidentally, the lipase or protease may be used a commercially available product as such in a natural form or as an immobilized enzyme, and it may be used alone or in admixture of two or more kinds. Also, it may be used by previously removing an enzyme-immobilizing agent contained in the commercially available product.

The above-mentioned lipase or protease may be used after subjecting a commercially available product in a natural form or an immobilized enzyme to chemical treatment or physical treatment.

As the above-mentioned chemical treatment or physical treatment method, there may be specifically mentioned, for example, a method in which a lipase or protease is dissolved in a buffer (an organic solvent may exist therein depending on necessity), and freeze-dried as such or after stirring, etc. Incidentally, freeze-drying means a method in which an aqueous solution or a substance containing a water component is rapidly frozen at a temperature of a freezing point or lower, and water is removed according to sublimation by reducing a pressure to a water vapor pressure of the frozen product or lower to dry the substance (for example, see Non-Patent Literature 3). Incidentally, according to the treatment, catalyst activity (reactivity or selectivity, etc.) can be improved.

The above-mentioned buffer may be mentioned, for example, an aqueous solution of an inorganic acid salt such as an aqueous sodium phosphate solution, an aqueous potassium phosphate solution, etc.; an aqueous solution of an organic acid salt such as an aqueous sodium acetate solution, an aqueous ammonium acetate solution, an aqueous sodium citrate solution, etc., preferably an aqueous sodium phosphate solution, an aqueous potassium phosphate solution or an aqueous ammonium acetate solution is used. Incidentally, these buffers may be used singly or in admixture of two or more kinds.

A concentration of the above-mentioned buffer is preferably 0.01 to 2 mol/L, more preferably 0.05 to 0.5 mol/L, and a pH of the buffer is preferably 4 to 9, more preferably 7 to 8.5.

An amount of the buffer to be used at the time of freeze-drying is not particularly limited so long as it is a concentration that the lipase or protease is completely dissolved, and it is preferably 10 ml to 1000 ml, more preferably 10 ml to 100 ml based on 1 g of the lipase or protease.

An amount of the above-mentioned lipase or protease to be used is preferably 0.1 to 1000 mg, more preferably 1 to 200 mg based on 1 g of Compound (I).

The reaction of the present invention can be carried out in the presence of a lipase or a protease in an organic solvent. During the reaction of the present invention, the lipase or protease pertains to the reaction by presenting substantially in a suspended state in the reaction mixture, and it may be dissolved therein without any problem. Incidentally, the terms "in an organic solvent" in the present invention mean the state in which a reaction solvent to be used in hydrolysis is an organic solvent, and a liquid portion dissolved in the organic solvent, except for a lipase or protease (which may sometimes include an immobilizing agent) and a product precipitated as crystals, etc., does not cause phase separation from the reaction system (that is, a state in which water (it may contain an inorganic salt or organic salt mentioned hereinbelow), a substrate and an organic solvent comprises single phase).

As water to be used in the reaction of the present invention, purified water such as deionized water, distilled water, etc. is generally used, and the water may contain an inorganic salt such as sodium phosphate, potassium phosphate, etc., or an organic salt such as sodium acetate, ammonium acetate, sodium citrate, etc. An amount of these inorganic salts and organic salts to be used is preferably in an amount of 0.01 to 10 mol/L, more preferably 0.1 to 1 mol/L based on the amount of water. Incidentally, the above-mentioned inorganic salt or organic salt is previously dissolved in water to prepare a buffer and the buffer may be used in the reaction without any problem.

An amount of the above-mentioned water is an amount equal to or less than the solubility (an amount capable of dissolving) of water in an organic solvent to be used (if the amount exceeds the solubility, phase separation of the liquid portion occurs), and an upper limit thereof may somewhat vary depending on the kind of Compound (I), and preferably 0.5 to 10 mol, more preferably 0.5 to 5.0 mol, further preferably 1.0 to 3.0 mol, particularly preferably 1.5 to 2.5 mol based on 1 mol of Compound (I). Incidentally, whereas it may vary deepening on the kind of Compound (I), when an amount of the water to be used exceeds 10 mol based on 1 mol of Compound (I), undesirable states occurs, for example, self-hydrolysis of Compound (I) which lowers an optical purity, elongation of the reaction time due to suspended state in which a slight amount of water does not dissolve in an organic solvent (a state in which phase separation occurs at the liquid portion), etc., so that the amount of the water to be used is preferably adjusted to an amount of the solubility of water in an organic solvent or less, preferably 10 mol or less.

As the above-mentioned organic solvent, there may be mentioned, for example, an aliphatic hydrocarbon such as n-pentane, n-hexane, n-heptane, n-octane, cyclopentane, cyclohexane and cyclopentane, etc.; an aromatic hydrocarbon such as benzene, toluene and xylene, etc.; an ether such as diethyl ether, t-butyl methyl ether, diisopropyl ether, cyclopentyl methyl ether, tetrahydrofuran and 1,4-dioxane, etc.; a ketone such as acetone and methyl ethyl ketone, etc., preferably n-hexane, n-heptane, cyclopentane, cyclohexane, toluene, diisopropyl ether, t-butyl methyl ether, cyclopentyl methyl ether and tetrahydrofuran, more preferably n-hexane, cyclohexane, toluene, diisopropyl ether, t-butyl methyl ether and cyclopentyl methyl ether, particularly preferably cyclohexane, toluene and/or t-butyl methyl ether is/are used. Incidentally, these organic solvents may be used singly or in admixture of two or more kinds.

An amount of the above-mentioned organic solvent to be used is preferably 2 to 200 mL, more preferably 5 to 80 mL based on 1 g of Compound (I). A ratio of the above-mentioned water and the organic solvent is not particularly limited, and an amount of water to be used may be an amount of the solubility of water in an organic solvent or less (that is, an amount which saturates in an organic solvent or less).

The reaction of the present invention is desirably carried out in the presence of a surfactant. As the surfactant to be used, there may be mentioned, for example, a nonionic surfactant such as polyethylene glycol, polyvinylpyrrolidone, polyethylene lauryl ether, polyethylene cetyl ether, polyoxyethylene octylphenyl ether, etc.; an amphoteric surfactant such as 3-[(3-chloroamidopropyl)-dimethylammonio]-2-hydroxy-1-propanesulfonate, 3-[(3-chloroamidopropyl)-dimethylammonio]-1-propanesulfonate, etc.; an anionic surfactant such as sodium dioctylsulfosuccinate, sodium dodecylsulfonate, tris(hydroxymethyl)aminomethane-dodecyl sulfate, etc.; a cationic surfactant such as cetyl trimethyl ammonium bromide or cetyl dimethylethyl ammonium bromide, etc., preferably a nonionic surfactant, more preferably polyethylene glycol, polyethylene cetyl ether, polyoxyethylene octylphenyl ether, particularly preferably polyoxyethylene octylphenyl ether is used. Incidentally, these surfactants may be used singly or in admixture of two or more kinds.

An amount of the above-mentioned surfactant to be used is preferably 10 to 1000 mg, more preferably 50 to 200 mg based on 1 g of Compound (I).

The reaction of the present invention can be carried out by the method, for example, in which Compound (I), a lipase or a protease, water (if necessary, it may contain an inorganic salt or an organic salt) and an organic solvent are mixed and reacted with stirring, etc. A reaction temperature at that time is preferably 0 to 80° C., more preferably 10 to 50° C., particularly preferably 30 to 45° C., and a reaction pressure is not particularly limited. Incidentally, during the reaction, lipase or protease is substantially in a suspended state, and depending on a kind of Compound (I), Compound (I) is precipitated as a white solid in some cases with the progress of the reaction, but these suspension or precipitation does not cause any effect on the reaction.

With regard to Compound (II) and Compound (III) obtained by the reaction of the present invention, when Compound (II) is precipitated after completion of the reaction, then, Compound (II) can be obtained, for example, by adding a suitable organic solvent (for example, acetonitrile, acetone, etc.) to the reaction mixture and filtered, and Compound (III) can be obtained by concentrating the organic layer. Also, when Compound (II) is not precipitated after completion of the reaction, Compound (II) can be obtained, for example, by adjusting a pH of the mixture, extracting Compound (II) with water, further adjusting a pH of the extract again and extracting with an organic solvent, and concentrating the obtained organic layer. Compound (III) can be obtained by concentrating the organic layer which has been separated at the time of extracting Compound (II) with water. Incidentally, the obtained Compound (II) and Compound (III) may be further purified by the conventionally known method such as crystallization, recrystallization, distillation, column chromatography, etc.

In the present invention, each compound is separated from a mixture of an optically active (S or R)-α-amino acid represented by the above-mentioned formula (II) formed by the reaction with water and an optically active (R or S)-α-amino acid ester represented by the above-mentioned formula (III), and the obtained optically active (R or S)-α-amino acid ester is reacted with an acid to prepare an acid salt of the optically active (R or S)-α-amino acid ester.

As the acid usable for the above-mentioned reaction, there may be mentioned, for example, hydrochloric acid, sulfuric acid, acetic acid, p-toluenesulfonic acid, oxalic acid, formic acid and carbonic acid, preferably hydrochloric acid is used.

An amount of the above-mentioned acid to be used is preferably 0.5 to 2.0 mol, more preferably 0.9 to 1.5 mol based on 1 mol of Compound (III).

Also, the above-mentioned reaction is preferably carried out in an organic solvent. Such an organic solvent may be mentioned, for example, at least one organic solvent selected from the group consisting of an ether, a ketone, an ester, an aliphatic hydrocarbon and an aromatic hydrocarbon.

An amount of the above-mentioned organic solvent to be used is preferably 1 to 50 mL, more preferably 3 to 20 mL based on 1 g of Compound (III).

The above-mentioned reaction can be carried out, for example, by mixing Compound (III), an acid and an organic solvent, and reacting them with stirring, etc. A reaction temperature at that time is preferably −20 to 80° C., more preferably −10 to 50° C., particularly preferably −5 to 40° C., and a reaction pressure is not particularly limited.

An acid salt of an optically active (R or S)-α-amino acid ester obtained by the reaction of the present invention can be further purified by a usual method such as crystallization, recrystallization, distillation, column chromatography, etc.

EXAMPLES

Next, the present invention is specifically explained by referring to Examples, but the scope of the present invention is not limited by these Examples.

Reference Example 1

Synthesis of ethyl 2-amino-3-phenylpropionate (racemic mixture)

To 10.0 mL (171 mmol) of ethanol were added 2.00 g (12.1 mmol) of 2-amino-3-phenylpropionic acid (racemic mixture) and 1.42 g (14.5 mmol) of conc. sulfuric acid, and they were reacted with stirring at 60° C. for 4 hours. After completion of the reaction, the obtained reaction mixture was concentrated under reduced pressure, and then, 6 mol/L aqueous sodium hydroxide solution was added to the mixture to adjust a pH of the reaction mixture to 8.5. Then, 10 mL of t-butyl methyl ether and 4 mL of water were added to the mixture to extract the product, and the organic layer was dried over anhydrous magnesium sulfate. After filtration, the filtrate was concentrated under reduced pressure to obtain 2.34 g (Isolation yield based on 2-amino-3-phenylpropionic acid (racemic mixture): 100%) of ethyl 2-amino-3-phenylpropionate (racemic mixture) as colorless liquid.

Incidentally, physical properties of the ethyl 2-amino-3-phenylpropionate (racemic mixture) were as follows.

$^1$H-NMR (δ (ppm), CDCl$_3$): 1.22 (t, 3H, J=7.1 Hz), 2.85 (dd, 1H, J=7.8, 13.5 Hz), 3.06 (dd, 1H, J=5.4, 13.5 Hz), 3.69 (dd, 1H, J=5.4, 7.8 Hz), 4.14 (q, 2H, J=7.1 Hz), 7.17-7.30 (m, 5H) $^{13}$C-NMR (δ (ppm), CDCl$_3$): 14.2, 41.2, 55.9, 60.8, 126.7, 128.5, 129.3. 137.4, 175.0

MS (CI, i-C$_4$H$_{10}$) m/z: 194 (MH$^+$)

Example 1

Synthesis of (S)-2-amino-3-phenylpropionic acid and ethyl (R)-2-amino-3-phenylpropionate To 1.00 mL of t-butyl methyl ether saturated with water were added 100 mg (0.517 mmol) of ethyl 2-amino-3-phenylpropionate (racemic mixture) and 20.0 mg of a lipase (AMANO LIPASE PS (Trade name); available from Aldrich Corporation) originated from *Burkholderia cepacia* (*Pseudomonas cepacia*), and the mixture was reacted at 30° C. with stirring. After 156 hours, 0.5 mL of acetone was added to the reaction mixture and the resulting mixture was filtered to obtain 36.1 mg (Isolation yield based on ethyl 2-amino-3-phenylpropionate (racemic mixture)=42.2%) of (S)-2-amino-3-phenylpropionic acid as a mixture with the lipase.

The (S)-2-amino-3-phenylpropionic acid was led to ethyl (S)-2-(2-furoylamino)-3-phenylpropionate according to the conventional manner, and when an optical purity thereof was measured by using high performance liquid chromatography which uses an optically active column, it was 96.5% ee.

The ethyl (R)-2-amino-3-phenylpropionate was led to ethyl (R)-2-(2-furoylamino)-3-phenylpropionate according to the conventional manner, and when an optical purity thereof was measured by using high performance liquid chromatography which uses an optically active column, it was 89.5% ee.

Incidentally, an E value in this reaction was 170.
Analytical conditions of high performance liquid chromatography;

Optically active ethyl 2-(2-furoylamino)-3-phenylpropionate
Column: CHIRALCEL OJ-H (0.46 cmΦ×25 cm, available from DAICEL CHEMICAL INDUSTRIES, LTD.)
Solvent: hexane/isopropyl alcohol (=8/2 (Volume ratio))
Flow rate: 0.5 mL/min
Temperature: 30° C.
Wavelength: 220 nm Also, physical properties of the (S)-2-amino-3-phenylpropionic acid were as follows.

$^1$H-NMR (δ (ppm), CD$_3$OD): 3.12 (dd, 1H, J=8.0, 14.5 Hz), 3.29 (dd, 1H, J=5.2, 14.5 Hz), 3.99 (dd, 1H, J=5.2, 8.0 Hz), 7.32-7.45 (m, 5H)

$^{13}$C-NMR (δ (ppm), CD$_3$OD): 39.2, 58.9, 130.5, 132.0, 132.2, 138.0, 176.8

MS (CI, i-C$_4$H$_{10}$) m/z: 166 (MH$^+$)

Specific Rotation: [α]$^{25}_D$ −26.5° (c 0.5, H$_2$O)

Incidentally, a specific rotation of the obtained optically active 2-amino-3-phenylpropionic acid and a sign ([α]$^{20}_D$ −33.4 to −35.0° (c2, H$_2$O)) of the specific rotation of the (S)-2-amino-3-phenylpropionic acid mentioned in a brochure published by Wako Pure Chemical Industries, Ltd. are compared to each other so that the absolute configuration was determined.

Physical properties of the ethyl (R)-2-amino-3-phenylpropionate were the same as those shown in Reference example 1.

Analytical conditions of high performance liquid chromatography;
Optically active ethyl 2-(2-furoylamino)-3-phenylpropionate
Column: CHIRALCEL OJ-H (0.46 cmΦ×25 cm, available from DAICEL CHEMICAL INDUSTRIES, LTD.)
Solvent: hexane/isopropyl alcohol (=8/2 (Volume ratio))
Flow rate: 0.5 mL/min
Temperature: 30° C.
Wavelength: 220 nm Also, physical properties of the (S)-2-amino-3-phenylpropionic acid were the same as those shown in Example 1.

Physical properties of the ethyl (R)-2-amino-3-phenylpropionate were the same as those shown in Reference example 1.

Reference Example 2

Synthesis of ethyl 2-amino-3-(3-fluorophenyl)propionate (racemic mixture)

To 10.0 mL (171 mmol) of ethanol were added 2.00 g (10.9 mmol) of 2-amino-3-(3-fluorophenyl)propionic acid (racemic mixture) and 1.29 g (13.1 mmol) of conc. sulfuric acid, and the mixture was reacted at 60° C. for 4 hours with stirring. After completion of the reaction, the obtained reaction mixture was concentrated under reduced pressure, and then, 6 mol/L aqueous sodium hydroxide solution was added to the mixture to adjust a pH of the reaction mixture to 8.5. Then, 10 mL of ethyl acetate and 4 mL of water were added to the mixture to extract the desired product, and the organic layer was dried over anhydrous magnesium sulfate. After filtration, the filtrate was concentrated under reduced pressure to obtain 1.97 g (Isolation yield based on 2-amino-3-(3-fluorophenyl)propionic acid (racemic mixture): 85.3%) of ethyl 2-amino-3-(3-fluorophenyl)propionate (racemic mixture) as a colorless liquid.

Incidentally, physical properties of the ethyl 2-amino-3-(3-fluorophenyl)propionate (racemic mixture) were as follows.

$^1$H-NMR (δ (ppm), CDCl$_3$): 1.25 (t, 3H, J=7.1 Hz), 2.88 (dd, 1H, J=7.8, 13.6 Hz), 3.07 (dd, 1H, J=5.5, 13.6 Hz), 3.71 (dd, 1H, J=5.5, 7.8 Hz), 4.17 (q, 2H, J=7.1 Hz), 6.91-7.00 (m, 3H), 7.26 (m, 1H)

$^{13}$C-NMR (δ (ppm), CDCl$_3$): 14.2, 40.8, 55.7, 61.1, 113.7, 113.8, 116.1, 116.3, 125.01, 125.02, 129.9, 130.0, 139.9, 140.0, 161.9, 163.9, 174.7

MS (CI, i-C$_4$H$_{10}$) m/z: 212 (MH$^+$)

Example 2

Synthesis of (S)-2-amino-3-(3-fluorophenyl)propionic acid and ethyl (R)-2-amino-3-(3-fluorophenyl)propionate To 1.0 mL of t-butyl methyl ether saturated with water were added 100 mg (0.473 mmol) of ethyl 2-amino-3-(3-fluorophenyl)propionate (racemic mixture) and 30.0 mg of a lipase (AMANO LIPASE PS (Trade name); available from ALDRICH CORPORATION) originated from *Burkholderia cepacia* (*Pseudomonas cepacia*), and reacted at 30° C. After 48 hours, 0.5 mL of acetone was added to the reaction mixture and the resulting mixture was filtered to obtain 31.1 mg (Isolation yield based on ethyl 2-amino-3-(3-fluorophenyl) propionate (racemic mixture)=35.9%) of (S)-2-amino-3-(3-fluorophenyl)propionic acid as a mixture with the lipase.

(S)-2-amino-3-(3-fluorophenyl)propionic acid was led to ethyl (S)-3-(3-fluorophenyl)-2-(2-furoylamino)propionate according to the conventional manner, and when its optical purity was measured by using high performance liquid chromatography which uses an optically active column, it was 98.0% ee.

Ethyl (R)-2-amino-3-(3-fluorophenyl)propionate was led to ethyl (R)-3-(3-fluorophenyl)-2-(2-furoylamino)propionate according to the conventional manner, and when its optical purity was measured by using high performance liquid chromatography which uses an optically active column, it was 82.8% ee.

Incidentally, the E value in this reaction was 258.
Analytical conditions of high performance liquid chromatography;
Optically active ethyl 3-(3-fluorophenyl)-2-(2-furoylamino) propionate
Column: CHIRALCEL OJ-H (0.46 cmΦ×25 cm, available from DAICEL CHEMICAL INDUSTRIES, LTD.)
Solvent: hexane/isopropyl alcohol (=9/1 (Volume ratio))
Flow rate: 0.5 mL/min
Temperature: 30° C.
Wavelength: 220 nm Also, physical properties of the (S)-2-amino-3-(3-fluorophenyl)propionic acid were as follows.

$^1$H-NMR (δ (ppm), CD$_3$OD): 3.02 (dd, 114, J=8.6, 14.6 Hz), 3.31 (dd, 1H, J=4.5, 14.6 Hz), 3.77 (dd, 1H, J=4.5, 8.6 Hz), 7.00 (m, 1H), 7.08 (m, 1H), 7.12 (m, 1H), 7.34 (m, 1H)

$^{13}$C-NMR (δ (ppm), CD$_3$OD): 37.9, 57.3, 115.1, 115.2, 117.1, 117.3, 126.32, 126.34, 131.6, 131.7, 140.0, 140.1, 163.5, 165.5, 173.4

MS (CI, i-C$_4$H$_{10}$) m/z: 184 (MH$^+$)

Elemental analysis; Calcd: C, 59.01%; H, 5.50%; N, 7.65%.

Found: C, 57.86%; H, 5.46%; N, 7.90%.

Physical properties of the ethyl (R)-2-amino-3-(3-fluorophenyl)propionate were the same as those shown in Reference example 2.

Reference Example 3

Synthesis of ethyl 2-amino-3-(4-fluorophenyl)propionate (racemic mixture)

To 10.0 mL (171 mmol) of ethanol were added 2.00 g (10.9 mmol) of 2-amino-3-(4-fluorophenyl)propionic acid (racemic mixture) and 1.29 g (13.1 mmol) of conc. sulfuric acid, and the mixture was reacted at 60° C. for 4 hours with stirring. After completion of the reaction, the obtained reaction mixture was concentrated under reduced pressure, and then, 6 mol/L aqueous sodium hydroxide solution was added to the mixture to adjust a pH of the reaction mixture to 8.5. Then, 10 mL of t-butyl methyl ether and 4 mL of water were added to the mixture to extract the desired product, and the organic layer was dried over anhydrous magnesium sulfate. After filtration, the filtrate was concentrated under reduced pressure to obtain 1.95 g (Isolation yield based on 2-amino-3-(4-fluorophenyl)propionic acid (racemic mixture): 84.4%) of ethyl 2-amino-3-(4-fluorophenyl)propionate (racemic mixture) as a colorless liquid.

Incidentally, physical properties of the ethyl 2-amino-3-(4-fluorophenyl)propionate (racemic mixture) were as follows.

$^1$H-NMR ($\delta$ (ppm), CDCl$_3$): 1.23 (t, 3H, J=7.1 Hz), 2.96 (dd, 1H, J=7.6, 13.7 Hz), 3.04 (dd, 1H, J=5.5, 13.7 Hz), 3.68 (dd, 1H, J=5.5, 7.6 Hz), 4.16 (q, 2H, J=7.1 Hz), 6.99 (m, 2H), 7.17 (m, 2H)

$^{13}$C-NMR ($\delta$ (ppm), CDCl$_3$): 14.2, 40.2, 55.9, 61.0, 115.2, 115.4, 130.75, 130.81, 132.97, 133.00, 160.9, 162.9, 174.9

MS (CI, i-C$_4$H$_{10}$) m/z: 212 (MH$^+$)

Elemental analysis; Calcd: C, 62.55%; H, 6.68%; N, 6.63%.

Found: C, 61.19%; H, 6.54%; N, 6.51%.

Example 3

Synthesis of (S)-2-amino-3-(4-fluorophenyl)propionic acid and ethyl (R)-2-amino-3-(4-fluorophenyl)propionate To 1.0 mL of t-butyl methyl ether saturated with water were added 100 mg (0.473 mmol) of ethyl 2-amino-3-(4-fluorophenyl)propionate (racemic mixture) and 30.0 mg of a lipase (AMANO LIPASE PS (Trade name); available from Aldrich Corporation) originated from *Burkholderia cepacia* (*Pseudomonas cepacia*), and the mixture was reacted at 30° C. with stirring. After 56 hours, 0.5 mL of acetone was added to the reaction mixture and the resulting mixture was filtered to obtain 36.7 mg (Isolation yield based on ethyl 2-amino-3-(4-fluorophenyl)propionate (racemic mixture)=42.3%) of (S)-2-amino-3-(4-fluorophenyl)propionic acid as a mixture with the lipase.

(S)-2-amino-3-(4-fluorophenyl)propionic acid was led to ethyl (S)-3-(4-fluorophenyl)-2-(2-furoylamino)propionate according to the conventional manner, and when its optical purity was measured by using high performance liquid chromatography which uses an optically active column, it was 99.1% ee.

Ethyl (R)-2-amino-3-(4-fluorophenyl)propionate was led to ethyl (R)-3-(4-fluorophenyl)-2-(2-furoylamino)propionate according to the conventional manner, and when its optical purity was measured by using high performance liquid chromatography which uses an optically active column, it was 91.2% ee.

Incidentally, the E value in this reaction was 698.

Analytical conditions of high performance liquid chromatography;

Optically active ethyl 3-(4-fluorophenyl)-2-(2-furoylamino)propionate

Column: CHIRALCEL OJ-H (0.46 cm$\Phi$×25 cm, available from DAICEL CHEMICAL INDUSTRIES, LTD.)

Solvent: hexane/isopropyl alcohol (=8/2 (volume ratio))

Flow rate: 0.5 mL/min

Temperature: 30° C.

Wavelength: 220 nm

Also, physical properties of the (S)-2-amino-3-(4-fluorophenyl)propionic acid were as follows.

$^1$H-NMR ($\delta$ (ppm), CD$_3$OD): 3.00 (dd, 1H, J=8.5, 14.7 Hz), 3.27 (dd, 1H, J=4.5, 14.7 Hz), 3.74 (dd, 1H, J=4.5, 8.5 Hz), 7.05 (m, 2H), 7.31 (m, 2H)

$^{13}$C-NMR ($\delta$ (ppm), CD$_3$CD): 37.5, 57.6, 116.5, 116.6, 132.2, 132.3, 133.2, 133.3, 162.9, 164.6, 173.6

MS (CI, i-C$_4$H$_{10}$) m/z: 184 (MH$^+$)

Elemental analysis; Calcd: C, 59.01%; H, 5.50%; N, 7.65%.

Found: C, 58.73%; H, 5.49%; N, 7.68%.

Physical properties of the ethyl (R)-2-amino-3-(4-fluorophenyl)propionate were the same as those shown in Reference example 3.

Reference Example 4

Synthesis of ethyl 2-amino-3-(4-bromophenyl)propionate (Racemic Mixture)

To 5.00 mL (85.7 mmol) of ethanol were added 1.00 g (4.10 mmol) of 2-amino-3-(4-bromophenyl)propionic acid (racemic mixture) and 482 mg (4.92 mmol) of conc. sulfuric acid, and the mixture was reacted with stirring at 60° C. for 4 hours. After completion of the reaction, the obtained reaction mixture was concentrated under reduced pressure, and then, 6 mol/L aqueous sodium hydroxide solution was added to the mixture to adjust a pH of the reaction mixture to 8.5. Then, 10 mL of t-butyl methyl ether and 4 mL of water were added to extract the desired product, and the organic layer was dried over anhydrous magnesium sulfate. After filtration, the filtrate was concentrated under reduced pressure to obtain 916 mg (Isolation yield based on 2-amino-3-(4-bromophenyl)propionic acid (racemic mixture): 82.5%) of ethyl 2-amino-3-(4-bromophenyl)propionate (racemic mixture) as colorless liquid.

Incidentally, physical properties of the ethyl 2-amino-3-(4-bromophenyl)propionate (racemic mixture) were as follows.

$^1$H-NMR ($\delta$ (ppm), CDCl$_3$) 1.25 (t, 3H, J=7.1 Hz), 2.83 (dd, 1H, J=7.7, 13.7 Hz), 3.03 (dd, 1H, J=5.5, 13.7 Hz), 3.68 (dd, 1H, J=5.5, 7.7 Hz), 7.08 (m, 2H), 7.42 (m, 2H)

$^{13}$C-NMR ($\delta$ (ppm), CDCl$_3$): 14.2, 40.4, 55.7, 61.1, 120.8, 131.1, 131.7, 136.3, 174.7

MS (CI, i-C$_4$H$_{10}$) m/z: 272 (MH$^+$)

Elemental analysis; Calcd: C, 48.55%; H, 5.19%; N, 5.15%.

Found: C, 47.71%; H, 5.21%; N, 5.06%.

Example 4

Synthesis of (S)-2-amino-3-(4-bromophenyl)propionic acid and ethyl (R)-2-amino-3-(4-bromophenyl)propionate To 1.0 mL of t-butyl methyl ether saturated with water were added 200 mg (0.735 mmol) of ethyl 2-amino-3-(4-bromophenyl)propionate (racemic mixture) and 30.0 mg of a lipase (AMANO LIPASE PS (Trade name); available from Aldrich Corporation) originated from *Burkholderia cepacia* (*Pseudomonas cepacia*), and the mixture was reacted with stirring at 30° C. After 56 hours, 0.5 mL of acetone was added to the reaction mixture and the resulting mixture was filtered to obtain 36.2 mg (Isolation yield based on ethyl 2-amino-3-(4-bromophenyl)propionate (racemic mixture)=40.4%) of (S)-2-amino-3-phenylpropionic acid as a mixture with the lipase.

(S)-2-amino-3-(4-bromophenyl)propionic acid was led to ethyl (S)-3-(4-bromophenyl)-2-(2-furoylamino)propionate according to the conventional manner, and when its optical purity was measured by using high performance liquid chromatography which uses an optically active column, it was 98.5% ee.

Ethyl (R)-2-amino-3-(4-bromophenyl)propionate was led to ethyl (R)-3-(4-bromophenyl)-2-(2-furoylamino)propionate according to the conventional manner, and when its optical purity was measured by using high performance liquid chromatography which uses an optically active column, it was 87.7% ee.

Incidentally, the E value in this reaction was 388.
Analytical conditions of high performance liquid chromatography;
Optically active ethyl 3-(4-bromophenyl)-2-(2-furoylamino)propionate
Column: CHIRALCEL OJ-H (0.46 cmΦ×25 cm, available from DAICEL CHEMICAL INDUSTRIES, LTD.)
Solvent: hexane/isopropyl alcohol (=8/2 (Volume ratio))
Flow rate: 0.5 mL/min
Temperature: 30° C.
Wavelength: 220 nm Also, physical properties of the (S)-2-amino-3-(4-bromophenyl)propionic acid were as follows.
$^1$H-NMR (δ (ppm), CD$_3$OD): 2.99 (dd, 1H, J=8.4, 14.6 Hz), 3.25 (dd, 1H, J=4.5, 14.6 Hz), 3.74 (dd, 1H, J=4.5, 8.4 Hz), 7.22 (m, 2H), 7.48 (m, 2H)
$^{13}$C-NMR (δ (ppm), CD$_3$OD): 37.7, 57.3, 122.2, 132.4, 133.0, 136.6, 173.5
MS (CI, i-C$_4$H$_{10}$) m/z: 244 (MH$^+$)
Elemental analysis; Calcd: C, 44.29%; H, 4.13%; N, 5.74%.
Found: C, 43.95%; H, 4.06%; N, 5.66%.

Physical properties of the ethyl (R)-2-amino-3-(4-bromophenyl)propionate were the same as those shown in Reference example 4.

Reference Example 5

Synthesis of ethyl 2-amino-3-(2-naphthyl)propionate (Racemic Mixture)

To 9.0 mL (154 mmol) of ethanol were added 1.80 g (8.36 mmol) of 2-amino-3-(naphthyl)propionic acid (racemic mixture) and 1.23 g (12.5 mmol) of conc. sulfuric acid, and the mixture was reacted with stirring at 60° C. for 6 hours. After completion of the reaction, the obtained reaction mixture was concentrated under reduced pressure, and then, 6 mol/L aqueous sodium hydroxide solution was added to the mixture to adjust a pH of the reaction mixture to 8.5. Then, 18 mL of t-butyl methyl ether and 4 mL of water were added to extract the desired product, and the organic layer was dried over anhydrous magnesium sulfate. After filtration, the filtrate was concentrated under reduced pressure to obtain 1.73 g (Isolation yield based on 2-amino-3-(2-naphthyl)propionic acid (racemic mixture): 85.0%) of ethyl 2-amino-3-(2-naphthyl)propionate (racemic mixture) as pale yellowish liquid.

Incidentally, physical properties of the ethyl 2-amino-3-(2-naphthyl)propionate (racemic mixture) were as follows.
$^1$H-NMR (δ (ppm), CDCl$_3$): 1.20 (t, 3H, J=7.1 Hz), 1.58 (s, 2H), 3.00 (dd; 1H, J=7.9, 13.5 Hz), 3.23 (dd, 1H, J=5.3, 13.5 Hz), 3.78 (dd, 1H, J=5.3, 7.9 Hz), 4.15 (q, 2H, J=7.1 Hz), 7.31 (dd, 1H, J=1.7, 8.4 Hz), 7.39-7.45 (m, 2H), 7.64 (m, 1H), 7.76-7.79 (m, 3H)
$^{13}$C-NMR (δ (ppm), CDCl$_3$): 14.2, 40.2, 55.9, 61.0, 115.2, 115.4, 130.75, 130.81, 132.97, 133.00, 160.9, 162.9, 174.9
MS (EI) m/z: 243 (M$^+$)
MS (CI, i-C$_4$H$_{10}$) m/z: 244 (MH$^+$)
Elemental analysis; Calcd: C, 74.05%; H, 7.04%; N, 5.76%.
Found: C, 72.89%; H, 6.72%; N, 5.58%.

Example 5

Synthesis of (S)-2-amino-3-(2-naphthyl)propionic acid and ethyl (R)-2-amino-3-(2-naphthyl)propionate To 2.0 mL of t-butyl methyl ether saturated with water were added 200 mg (0.822 mmol) of ethyl 2-amino-3-(2-naphthyl)propionate (racemic mixture) and 10.0 mg of a lipase (AMANO LIPASE PS (Trade name); available from Aldrich Corporation) originated from *Burkholderia cepacia* (*Pseudomonas cepacia*), and the mixture was reacted with stirring at 30° C. After 168 hours, the reaction mixture was filtered, and washed with 2.0 mL of t-butyl methyl ether to obtain 86.1 mg (Isolation yield based on ethyl 2-amino-3-(4-fluorophenyl)propionate (racemic mixture)=48.7%) of (S)-2-amino-3-(2-naphthyl)propionic acid as a mixture with the lipase.

Also, after filtration, the filtrate was concentrated under reduced pressure to obtain 110 mg (Isolation yield based on ethyl 2-amino-3-(2-naphthyl)propionate (racemic mixture)= 55.0%) of ethyl (R)-2-amino-3-(2-naphthyl)propionate as pale yellowish liquid.

(S)-2-amino-3-(2-naphthyl)propionic acid was led to ethyl (S)-2-(2-furoylamino)-3-(2-naphthyl)propionate according to the conventional manner, and when its optical purity was measured by using high performance liquid chromatography which uses an optically active column, it was 99.3% ee.

Ethyl (R)-2-amino-3-(2-naphthyl)propionate was led to ethyl (R)-2-(2-furoylamino)-2-(2-naphthyl)propionate according to the conventional manner, and when its optical purity was measured by using high performance liquid chromatography which uses an optically active column, it was 79.3% ee.

Incidentally, the E value in this reaction was 711.
Analytical conditions of high performance liquid chromatography;
Optically active ethyl 3-(2-furoylamino)-3-(2-naphthyl)propionate
Column: CHIRALCEL OJ-H (0.46 cmΦ×25 cm, available from DAICEL CHEMICAL INDUSTRIES, LTD.)
Solvent: hexane/isopropyl alcohol (=8/2 (Volume ratio))
Flow rate: 0.5 mL/min
Temperature: 30° C.
Wavelength: 220 nm Also, physical properties of the (S)-2-amino-3-(2-naphthyl)propionic acid were as follows.
$^1$H-NMR (δ (ppm), D$_2$O): 3.41 (dd, 1H, J=7.7, 14.6 Hz), 3.53 (dd, 1H, J=5.7, 14.6 Hz), 4.50 (dd, 1H, J=5.7, 7.7 Hz), 7.46 (d, 1H, J=8.4 Hz), 7.57-7.61 (m, 2H), 7.84 (s, 1H) 7.93-7.97 (m, 3H)
$^{13}$C-NMR (δ (ppm), D$_2$O): 38.6, 56.8, 129.4, 129.67, 130.0, 130.6, 131.4, 131.8, 134.4, 135.4, 136.1, 174.0

MS (EI) m/z: 215 (M$^+$)

MS (CI, i-C$_4$H$_{10}$) m/z: 216 (MH$^+$)

Physical properties of the ethyl (R)-2-amino-3-(2-naphthyl)propionate were the same as those shown in Reference example 5.

Reference Example 6

Synthesis of ethyl 2-amino-3-(3-indolyl)propionate (racemic mixture)

To 5.0 mL (85.6 mmol) of ethanol were added 1.00 g (4.90 mmol) of 2-amino-3-(3-indolyl)propionic acid (racemic mixture) and 0.96 g (9.79 mmol) of conc. sulfuric acid, and the mixture was reacted with stirring at 60° C. for 4 hours. After completion of the reaction, the obtained reaction mixture was concentrated under reduced pressure, and then, 6 mol/L aqueous sodium hydroxide solution was added to the mixture to adjust a pH of the reaction mixture to 8.5. Then, 10 mL of t-butyl methyl ether and 4 mL of water were added to extract the desired product, and the organic layer was dried over anhydrous magnesium sulfate. After filtration, the filtrate was concentrated under reduced pressure to obtain 0.97 g (Isolation yield based on 2-amino-3-(3-indolyl)propionic acid (racemic mixture): 85.1%) of ethyl 2-amino-3-(3-indolyl)propionate (racemic mixture) as colorless liquid.

Incidentally, physical properties of the ethyl 2-amino-3-(3-indolyl)propionate (racemic mixture) were as follows.

$^1$H-NMR (δ (ppm), D$_2$O): 1.21 (t, 3H, J=7.0 Hz), 1.63 (s, 2H) 3.01 (dd, 1H, J=7.9, 14.4 Hz), 3.25 (dd, 1H, J=4.8, 14.4 Hz), 3.80 (dd, 1H, J=4.8, 7.9 Hz), 4.14 (q, 2H, J=7.0 Hz), 6.90 (s, 1H) 7.06-7.26 (m, 3H), 7.59 (d, 1H, J=7.9 Hz), 9.07 (s, 1H)

$^{13}$C-NMR (δ (ppm), CDCl$_3$): 14.1, 49.4, 55.0, 61.0, 110.6, 111.4, 118.6, 119.2, 121.8, 123.3, 127.5, 136.4, 175.4

MS (EI) m/z: 232 (M$^+$)

MS (CI, i-C$_4$H$_{10}$) m/z: 233 (MH$^+$)

Example 6

Synthesis of (S)-2-amino-3-(3-indolyl)propionic acid and ethyl (R)-2-amino-3-(3-indolyl)propionate To 4.0 mL of t-butyl methyl ether saturated with water were added 200 mg (0.822 mmol) of ethyl 2-amino-3-(3-indolyl)propionate (racemic mixture) and 10.0 mg of a lipase (AMANO LIPASE PS (Trade name); available from Aldrich Corporation) originated from *Burkholderia cepacia* (*Pseudomonas cepacia*), and the mixture was reacted with stirring at 30° C. After 108 hours, the reaction mixture was filtered, and washed with 2.0 mL of t-butyl methyl ether to obtain 78.3 mg (Isolation yield based on ethyl 2-amino-3-(3-indolyl)propionate (racemic mixture)=44.5%) of (S)-2-amino-3-(3-indolyl)propionic acid as a mixture with the lipase.

Also, after filtration, the filtrate was concentrated under reduced pressure to obtain 106 mg (Isolation yield based on ethyl 2-amino-3-(3-indolyl)propionate (racemic mixture)= 53.0%) of ethyl (R)-2-amino-3-(3-indolyl)propionate as colorless liquid.

(S)-2-amino-3-(3-indolyl)propionic acid was led to ethyl (S)-2-(2-fluorophenyl)-3-(3-indolyl)propionate according to the conventional manner, and when its optical purity was measured by using high performance liquid chromatography which uses an optically active column, it was 98.7% ee.

Ethyl (R)-2-amino-3-(3-indolyl)propionate was led to ethyl (R)-2-(2-fluorophenyl)-3-(3-indolyl)propionate according to the conventional manner, and when its optical purity was measured by using high performance liquid chromatography which uses an optically active column, it was 81.8% ee.

Incidentally, the E value in this reaction was 392.

Analytical conditions of high performance liquid chromatography;

Optically active ethyl 2-(2-furoylamino)-3-(3-indolyl)propionate

Column: CHIRALCEL OJ-H (0.46 cmΦ×25 cm, available from DAICEL CHEMICAL INDUSTRIES, LTD.)

Solvent: hexane/isopropyl alcohol (=8/2 (Volume ratio))

Flow rate: 1.0 mL/min

Temperature: 30° C.

Wavelength: 220 nm

Also, physical properties of the (S)-2-amino-3-(3-indolyl) propionic acid were as follows.

$^1$H-NMR (δ (ppm), D$_2$O): 3.43 (dd, 1H, J=7.0, 15.4 Hz), 3.50 (dd, 1H, J=5.5, 15.4 Hz), 4.40 (dd, 1H, J=5.5, 7.0 Hz), 7.21-7.69 (m, 5H)

$^{13}$C-NMR (δ (ppm), D$_2$O): 29.2, 56.8, 109.7, 115.6, 121.8, 123.1, 125.8, 129.0, 130.1, 139.9, 175.1

MS (EI) m/z: 204 (M$^+$)

MS (CI, i-C$_4$H$_{10}$) m/z: 205 (MH$^+$)

Physical properties of the ethyl (R)-2-amino-3-(3-indolyl) propionate were the same as those shown in Reference example 6.

Example 7

Synthesis of (S)-2-amino-3-(4-fluorophenyl)propionic acid and ethyl (R)-2-amino-3-(4-fluorophenyl) propionate To 2.0 mL of t-butyl methyl ether saturated with water were added 200 mg (0.947 mmol) of ethyl 2-amino-3-(4-fluorophenyl)propionate (racemic mixture) and 1.0 mg of α-chymotrypsin, and the mixture was reacted with stirring at 30° C. After 84 hours, the reaction mixture was filtered to obtain 70.8 mg (Isolation yield based on ethyl 2-amino-3-(4-fluorophenyl)propionate (racemic mixture)=40.8%) of (S)-2-amino-3-(4-fluorophenyl)propionic acid. (S)-2-amino-3-(4-fluorophenyl)propionic acid was led to ethyl (S)-3-(4-fluorophenyl)-2-(2-furoylamino)propionate according to the conventional manner, and when its optical purity was measured by using high performance liquid chromatography which uses an optically active column, it was 98.1% ee.

Ethyl (R)-2-amino-3-(4-fluorophenyl)propionate was led to ethyl (R)-3-(4-fluorophenyl)-2-(2-furoylamino)propionate according to the conventional manner, and when its optical purity was measured by using high performance liquid chromatography which uses an optically active column, it was 83.3% ee.

Incidentally, the E value in this reaction was 271.

Analytical conditions of high performance liquid chromatography;

Optically active ethyl 3-(4-fluorophenyl)-2-(2-furoylamino) propionate

Column: CHIRALCEL OJ-H (0.46 cmΦ×25 cm, available from DAICEL CHEMICAL INDUSTRIES, LTD.)

Solvent: hexane/isopropyl alcohol (=9/1 (Volume ratio))

Flow rate: 0.5 mL/min

Temperature: 30° C.

Wavelength: 220 nm

Also, physical properties of the (S)-2-amino-3-(4-fluorophenyl)propionic acid were the same as those shown in Example 3.

Physical properties of the ethyl (R)-2-amino-3-(4-fluorophenyl)propionate were the same as those shown in Reference example 3.

Reference Example 7

Synthesis of ethyl 2-amino-4-methylpentanoate (Racemic Mixture)

To 40 mL (69 mmol) of ethanol were added 4.00 g (8.36 mmol) of 2-amino-4-methylpentanoic acid (racemic mixture) and 4.49 g (61.0 mmol) of conc. sulfuric acid, and the mixture was reacted with stirring at 60° C. for 6 hours. After completion of the reaction, the obtained reaction mixture was concentrated under reduced pressure, and then, 6 mol/L aqueous sodium hydroxide solution was added to the mixture to adjust a pH of the reaction mixture to 8.5. Then, 40 mL of methylene chloride and 10 mL of water were added to the reaction mixture to extract the desired product, and the organic layer was dried over anhydrous magnesium sulfate. After filtration, the filtrate was concentrated under reduced pressure to obtain 3.79 g (Isolation yield based on 2-amino-4-methylpentanoic acid (racemic mixture): 78.0%) of ethyl 2-amino-4-methylpentanoate (racemic mixture) as colorless liquid.

Incidentally, physical properties of the ethyl 2-amino-4-methylpentanoate (racemic mixture) were as follows.
$^1$H-NMR (δ (ppm), CDCl$_3$): 0.92-0.95 (m, 6H), 1.28 (t, 3H, J=7.1 Hz), 1.39-1.45 (m, 1H), 1.50 (s, 2H), 1.53-1.59 (m, 1H), 1.74-1.81 (m, 1H), 3.45 (dd, 1H, J=5.6, 8.7 Hz) 4.17 (q, 2H, J=7.1 Hz)
$^{13}$C-NMR (δ (ppm), CDCl$_3$): 14.2, 21.9, 23.0, 24.8, 44.2, 52.9, 60.7, 176.7
MS (CI, i-C$_4$H$_{10}$) m/z: 160 (MH$^+$)

Example 8

Synthesis of (S)-2-amino-4-methylpentanoic acid and ethyl (R)-2-amino-4-methyl-pentanoate To 2.0 mL of t-butyl methyl ether saturated with water were added 100 mg (0.63 mmol) of ethyl 2-amino-4-methylpentanoate (racemic mixture) and 1.0 mg of α-chymotrypsin, and the mixture was reacted with stirring at 30° C. After 64 hours, the reaction mixture was filtered, and washed with 2.0 mL of t-butyl methyl ether to obtain 37.1 mg (Isolation yield based on ethyl 2-amino-3-(4-fluorophenyl)propionate (racemic mixture)=45.0%) of (S)-2-amino-4-methylpentanoic acid.

Also, after filtration, the filtrate was concentrated under reduced pressure to obtain 50 mg (Isolation yield based on ethyl 2-amino-4-methylpentanoate (racemic mixture)= 50.0%) of ethyl (R)-2-amino-4-methylpentanoate as colorless liquid.

(S)-2-amino-4-methylpentanoic acid was led to ethyl (S)-2-benzoylamino-4-methylpentanoate according to the conventional manner, and when its optical purity was measured by using high performance liquid chromatography which uses an optically active column, it was 98.2% ee.

Ethyl (R)-2-amino-4-methylpentanoate was led to ethyl (R)-2-benzoylamino-4-methylpentanoate according to the conventional manner, and when its optical purity was measured by using high performance liquid chromatography which uses an optically active column, it was 88.8% ee.

Incidentally, the E value in this reaction was 323.
Analytical conditions of high performance liquid chromatography;

Optically active ethyl 2-benzoylamino-4-methylpentanoate
Column: CHIRALCEL OD-H (0.46 cmΦ×25 cm, available from DAICEL CHEMICAL INDUSTRIES, LTD.)
Solvent: hexane/isopropyl alcohol (=9/1 (Volume ratio))
Flow rate: 0.5 mL/min
Temperature: 30° C.
Wavelength: 220 nm Also, physical properties of the (S)-2-amino-4-methylpentanoic acid were as follows.
$^1$H-NMR (δ (ppm), D$_2$O):
0.96-1.01 (m, 6H), 1.74-1.90 (m, 3H), 4.11 (m, 1H)
$^{13}$C-NMR (δ (ppm), CD$_3$OD): 23.9, 24.5, 26.8, 41.6, 54.3, 175.2
MS (CI, i-C$_4$H$_{10}$) m/z: 132 (MH$^+$)
Elemental analysis; Calcd: C, 54.94%; H, 9.99%; N, 10.68%.
Found: C, 54.42%; H, 9.83%; N, 10.73%.

Physical properties of the ethyl (R)-2-amino-4-methylpentanoate were the same as those shown in Reference example 7.

Reference Example 8

Synthesis of ethyl 2-amino-3-(4-methoxyphenyl)propionate (racemic mixture)

To 6.0 mL (103 mmol) of ethanol were added 600 mg (3.07 mmol) of 2-amino-3-(4-methoxyphenyl)propionic acid (racemic mixture) and 603 mg (6.15 mmol) of conc. sulfuric acid, and the mixture was reacted with stirring at 60° C. for 4 hours. After completion of the reaction, the obtained reaction mixture was concentrated under reduced pressure, and then, 6 mol/L aqueous sodium hydroxide solution was added to the mixture to adjust a pH of the reaction mixture to 8.5. Then, 6 mL of t-butyl methyl ether and 2 mL of water were added to the reaction mixture to extract the desired product, and the organic layer was dried over anhydrous magnesium sulfate. After filtration, the filtrate was concentrated under reduced pressure to obtain 618 mg (Isolation yield based on 2-amino-3-(4-methoxyphenyl)propionic acid (racemic mixture): 90.1%) of ethyl 2-amino-3-(4-methoxyphenyl)propionate (racemic mixture) as colorless liquid.

Incidentally, physical properties of the ethyl 2-amino-3-(4-methoxyphenyl)propionate (racemic mixture) were as follows,
$^1$H-NMR (δ (ppm), CDCl$_3$): 1.25 (t, 3H, J=7.1 Hz), 1.58 (s, 2H), 2.82 (dd, 1H, J=7.8, 13.7 Hz), 3.02 (dd, 1H, J=5.4, 13.7 Hz), 3.66 (dd, 1H, J=5.4, 7.8 Hz), 3.79 (s, 3H), 1.17 (q, 2H, J=7.1 Hz), 6.82-6.86 (m, 2H), 7.10-7.12 (m, 2H) $^{13}$C-NMR (δ (ppm), CDCl$_3$): 14.2, 40.3, 55.3, 56.1, 60.9, 114.0, 129.3, 130.3, 158.6, 175.1
MS (CI, i-C$_4$H$_{10}$) m/z: 224 (MH$^+$)
Elemental analysis; Calcd: C, 64.55%; H, 7.67%; N, 6.27%.
Found: C, 64.27%; H, 7.27%; N, 6.17%.

Example 9

Synthesis of (S)-2-amino-3-(4-methoxyphenyl)propionic acid and ethyl (R)-2-amino-3-(4-methoxyphenyl)propionate To 4.0 mL of t-butyl methyl ether saturated with water were added 200 mg (0.900 mmol) of ethyl 2-amino-3-(4-methoxyphenyl)propionate (racemic mixture) and 10.0 mg of a lipase (AMANO LIPASE PS (Trade name); available from ALDRICH CORPORATION) originated from *Burkholderia* cepacia (*Pseudomonas cepacia*), and the mixture was reacted with stirring at 30° C. After 96 hours, the reaction mixture was filtered, and washed with 2.0 mL of t-butyl methyl ether to obtain 90.0 mg (Isolation yield based on ethyl 2-amino-3-(4-fluorophenyl)propionate (racemic mixture)=51.4%) of (S)-2-amino-3-(4-methoxyphenyl)propionic acid as a mixture with the lipase.

Also, after filtration, the filtrate was concentrated under reduced pressure to obtain 100 mg (Isolation yield based on ethyl 2-amino-3-(4-methoxyphenyl)propionate (racemic mixture)=50.0%) of ethyl (R)-2-amino-3-(4-methoxyphenyl)propionate as pale yellowish liquid.

(S)-2-amino-3-(4-methoxyphenyl)propionic acid was led to ethyl (S)-2-(2-furoylamino)-3-(4-methoxyphenyl)propionate according to the conventional manner, and when its optical purity was measured by using high performance liquid chromatography which uses an optically active column, it was 99.0% ee.

Ethyl (R)-2-amino-3-(4-methoxyphenyl)propionate was led to ethyl (R)-2-(2-furoylamino)-2-(4-methoxyphenyl)propionate according to the conventional manner, and when its optical purity was measured by using high performance liquid chromatography which uses an optically active column, it was 98.8% ee.

Incidentally, the E value in this reaction was 1042.
Analytical conditions of high performance liquid chromatography;
Optically active ethyl 3-(2-furoylamino)-3-(4-methoxyphenyl)propionate
Column: CHIRALCEL OJ-H (0.46 cmΦ×25 cm, available from DAICEL CHEMICAL INDUSTRIES, LTD.)
Solvent: hexane/isopropyl alcohol (=8/2 (Volume ratio))
Flow rate: 0.5 mL/min
Temperature: 30° C.
Wavelength: 220 nm Also, physical properties of the (S)-2-amino-3-(4-methoxyphenyl)propionic acid were as follows.
$^1$H-NMR (δ (ppm), CD$_3$OD):
3.20 (dd, 1H, J=7.4, 14.7 Hz), 3.30 (dd, 1H, J=5.6, 14.7 Hz), 4.36 (dd, 1H, J=5.6, 7.4 Hz), 5.06 (s, 3H), 7.00-7.02 (m, 2H), 7.27-7.29 (m, 2H)
$^{13}$C-NMR (δ (ppm), CD$_3$OD): 37.6, 57.0, 58.4, 117.6, 129.2, 133.7, 161.4, 174.1
MS (EI) m/z: 195 (M$^+$)
MS (CI, i-C$_4$H$_{10}$) m/z: 196 (MH$^+$)
Elemental analysis; Calcd: C, 61.53%; H, 6.71%; N, 7.18%.
Found: C, 60.40%; H, 6.56%; N, 7.04%.
Physical properties of the ethyl (R)-2-amino-3-(4-methoxyphenyl)propionate were the same as those shown in Reference example 8.

Example 10

Synthesis of ethyl (R)-2-amino-3-phenylpropionate hydrochloride

To 80 mL of t-butyl methyl ether saturated with water were added 4.00 g (20.7 mmol) of ethyl 2-amino-3-phenylpropionate (racemic mixture) and 800 mg of a lipase (AMANO LIPASE PS (Trade name); available from ALDRICH CORPORATION) originated from *Burkholderia cepacia* (*Pseudomonas cepacia*), and the mixture was reacted with stirring at 30° C. After 168 hours, the reaction mixture was filtered, dried over magnesium sulfate, filtered, concentrated under reduced pressure and 12 mL of cyclohexane was added to the residue. To the resulting cyclohexane solution was added 1.52 g (10.1 mmol of hydrochloric acid) of a hydrochloric acid-ethanol solution (hydrochloric acid content: 24.3% by weight) at 0° C. and the mixture was stirred at the same temperature for 1 hour. The reaction mixture was filtered to obtain 1.90 g (Yield based on ethyl 2-amino-3-phenylpropionate (racemic mixture)=40.0%) of ethyl (R)-2-amino-3-phenylpropionate hydrochloride as white crystals.

Ethyl (R)-2-amino-3-phenylpropionate hydrochloride was led to ethyl (R)-2-(2-furoylamino)-3-phenylpropionate according to the conventional manner, and when its optical purity was measured by using high performance liquid chromatography which uses an optically active column, it was 97.1% ee.
Analytical conditions of high performance liquid chromatography;
Optically active ethyl 3-(2-furoylamino)-3-(4-methoxyphenyl)propionate
Column: CHIRALCEL OJ-H (0.46 cmΦ×25 cm, available from DAICEL CHEMICAL INDUSTRIES, LTD.)
Solvent: hexane/isopropyl alcohol (=8/2 (Volume ratio))
Flow rate: 0.5 mL/min
Temperature: 30° C.
Wavelength: 220 nm Also, physical properties of the ethyl (R)-2-amino-3-phenylpropionate hydrochloride were as follows.
$^1$H-NMR (δ (ppm), CD$_3$OD): 1.27 (t, 3H, J=7.2 Hz), 3.26 (dd, 1H, J=7.3, 14.5 Hz), 3.33 (dd, 1H, J=6.2, 14.5 Hz), 4.30 (q, 4H, J=7.2 Hz) 4.40 (dd, 1H, J=6.2, 7.3 Hz), 7.30-7.47 (m, 5H) $^{13}$C-NMR (δ (ppm), CD$_3$OD): 16.0, 38.5, 57.0, 66.4, 130.9, 132.0, 132.2, 136.6, 172.4
MS (CI, i-C$_4$H$_{10}$) m/z: 194 (MH$^+$)
Elemental analysis; Calcd: C, 57.52%; H, 7.02%; N, 6.10%.
Found: C, 57.29%; H, 6.81%; N, 6.13%.

UTILIZABILITY IN INDUSTRY

The present invention relates to a process for simultaneously preparing an optically active (S or R)-α-amino acid and an optically active (R or S)-α-amino acid ester which is an antipode ester thereof from an α-amino acid ester (racemic mixture). The optically active α-amino acid and an ester thereof are useful compounds as a starting material or a synthetic intermediate of a physiologically active peptide or a lactam series antibiotics.

The invention claimed is:
1. A process for preparing an optically active (S or R)-α-amino acid represented by the formula (II):

wherein R represents an alkyl group, an alkenyl group, an alkynyl group, a cycloalkyl group, an aralkyl group, a heteroarylalkyl group, an aryl group or a heteroaryl group, each of which may have a substituent(s), and * represents an asymmetric carbon atom,
and an optically active (R or S)-α-amino acid ester represented by the formula (III):

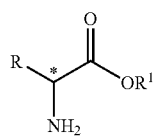

(III)

wherein R has the same meaning as defined above, $R^1$ represents an alkyl group which may have a substituent(s), and * represents an asymmetric carbon atom, provided that it has an opposite absolute configuration to that of the compound of the formula (II),
which comprises selectively reacting water with one of enantiomers of an α-amino acid ester which is a racemic mixture and represented by the formula (I):

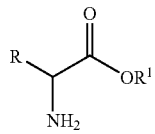

(I)

wherein R and $R^1$ have the same meanings as defined above,
in the presence of a lipase in an organic solvent in a single phase without causing phase separation from a reaction system.

2. The preparation process according to claim 1, wherein an amount of water to be used is 0.5 to 10 mol based on 1 mol of the α-amino acid ester which is a racemic mixture.

3. The preparation process according to claim 1, wherein the lipase is a lipase originated from *Burkholderia cepacia* (*Pseudomonas cepacia*).

4. The preparation process according to claim 1, wherein a buffer is present in the reaction system.

5. The preparation process according to claim 4, wherein the buffer is an aqueous solution of at least one material selected from the group consisting of sodium phosphate, potassium phosphate, sodium acetate, ammonium acetate and sodium citrate.

6. The preparation process according to claim 1, wherein the lipase has been lyophilized or freeze-dried in the presence of a buffer.

7. The preparation process according to claim 1, wherein at least one surfactant selected from the group consisting of a nonionic surfactant, an amphoteric surfactant, an anionic surfactant and a cationic surfactant is present in the reaction system.

8. The preparation process according to claim 1, wherein R is a benzyl group which may have a substituent(s).

9. The preparation process according to claim 1, wherein $R^1$ is a methyl group or an ethyl group each of which may have a substituent(s).

10. The preparation process according to claim 9, wherein the substituent(s) in $R^1$ is/are a halogen atom(s) or an alkoxy group(s).

11. The preparation process according to claim 1, wherein the organic solvent to be used is at least one organic solvent selected from the group consisting of an ether, a ketone, an ester, an aliphatic hydrocarbon and an aromatic hydrocarbon.

12. The preparation process according to claim 1, wherein the organic solvent is t-butyl methyl ether.

13. The preparation process according to claim 1, further comprising isolating each of the optically active (S or R)-α-amino acid represented by the formula (II):

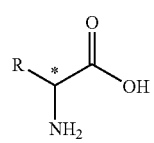

(II)

wherein R has the same meaning as defined above, and * represents an asymmetric carbon atom,
and the optically active (R or S)-α-amino acid ester represented by the formula (III):

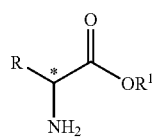

(III)

wherein R and $R^1$ have the same meanings as defined above, and * represents an asymmetric carbon atom, provided that it has an opposite absolute configuration to that of the compound of the formula (II),
formed by the reaction according to claim 1 from a mixture thereof.

14. The preparation process according to claim 1, wherein an amount of water to be used is 0.5 to 5.0 mol based on 1 mol of the α-amino acid ester which is a racemic mixture.

15. The preparation process according to claim 1, wherein an amount of water to be used is 0.5 to 3.0 mol based on 1 mol of the α-amino acid ester which is a racemic mixture.

16. The preparation process according to claim 1, wherein an amount of the organic solvent to be used is 2 to 200 mL based on 1 g of the α-amino acid ester which is a racemic mixture.

17. The preparation process according to claim 1, wherein an amount of the organic solvent to be used is 5 to 80 mL based on 1 g of the α-amino acid ester which is a racemic mixture.

* * * * *